United States Patent
Fujii et al.

(10) Patent No.: US 9,611,490 B2
(45) Date of Patent: Apr. 4, 2017

(54) BIOLOGICAL METHOD FOR PRODUCING CIS-5-HYDROXY-L-PIPECOLIC ACID

(71) Applicant: MicroBiopharm Japan Co., Ltd., Tokyo (JP)

(72) Inventors: Tadashi Fujii, Tokyo (JP); Keisuke Tamura, Tokyo (JP)

(73) Assignee: MicroBiopharm Japan Co., Ltd., Tokyo (JP)

( * ) Notice: Subject to any disclaimer, the term of this patent is extended or adjusted under 35 U.S.C. 154(b) by 0 days.

(21) Appl. No.: 14/407,576

(22) PCT Filed: Jun. 12, 2013

(86) PCT No.: PCT/JP2013/066218
§ 371 (c)(1),
(2) Date: Dec. 12, 2014

(87) PCT Pub. No.: WO2013/187438
PCT Pub. Date: Dec. 19, 2013

(65) Prior Publication Data
US 2015/0211035 A1    Jul. 30, 2015

(30) Foreign Application Priority Data
Jun. 13, 2012  (JP) ................ 2012-133876

(51) Int. Cl.
*C12P 17/12*       (2006.01)
*C12N 9/02*        (2006.01)

(52) U.S. Cl.
CPC ............ *C12P 17/12* (2013.01); *C12N 9/0004* (2013.01); *C12N 9/0071* (2013.01); *C12Y 114/11* (2013.01); *Y02P 20/52* (2015.11)

(58) Field of Classification Search
CPC ........................................ C12P 17/12
USPC ........................................ 435/122
IPC ........................................ C12P 17/12
See application file for complete search history.

(56) References Cited

FOREIGN PATENT DOCUMENTS

| EP | 1249494 A1 | 10/2002 |
|----|------------|---------|
| WO | 0148216 A1 | 7/2001 |
| WO | 2009139365 A1 | 11/2009 |

OTHER PUBLICATIONS

Fujii et al, "Biotransformation of L-Lysine to L-Pipecolic Acid Catalyzed by L-Lysine 6-Aminotransferase and Pyrroline-5-carboxylate Reductase," Biosci. Biotechnol. Biochem., vol. 66, No. 3, pp. 622-627 (2002).
Fujii et al, "Increase in the Rate of L-Pipecolic Acid Production Using lat-Expressing *Escherichia coli* by lysP and yeiE Amplification," Biosci. Biotechnol. Biochem., vol. 66, No. 9, pp. 1981-1984 (2002).
Klein et al, "A Simple Procedure for Selective Hydroxylation of L-Proline and L-Pipecolic Acid with Recominantly Expressed Proline Hydroxylases," Adv. Synth. Catal., vol. 353, pp. 1375-1383 (2011).
Aspartyl/Asparaginyl beta-hydroxylase [Segniliparus rugosus ATCC BAA-974], Online, 2011.
Earl, et al, "High quality draft genome sequence of Segniliparus rugosus CDC 945T=(ATCC BAA-974T)," Standards in Genomic Sciences, vol. 5, pp. 389-397 (2011).
Int'l Search Report and Written Opinion issued Jul. 9, 2013 in Int'l Application No. PCT/JP2013/066218.
Int'l Preliminary Report on Patentability issued Dec. 24, 2014 in Int'l Application No. PCT/JP2013/066218.
Office Action issued Aug. 10, 2016 in CN Application 201380030961.0.
Earl et al., "Segniliparus Rugosus ATCC BAA-974 cont1.186, Whole Genome Shotgun Sequence" Jan. 2011, downloaded from web page: www.ncbi.nlb.nih.gov/nuccore/316253105, Download date: Mar. 24, 2016, 4 pages.
Extended Search Report issued Apr. 11, 2016 in European Patent Application No. 13804143.9.

*Primary Examiner* — Tekchand Saidha
(74) *Attorney, Agent, or Firm* — Panitch Schwarze Belisario & Nadel LLP

(57) ABSTRACT

A method for producing cis-5-hydroxy-L-pipecolic acid is described. A gene recombinant microorganism enabling direct production of cis-5-hydroxy-L-pipecolic acid can be used in the method. Also described is a gene recombinant microorganism. In particular, it is described that a gene recombinant microorganism having DNAs encoding proteins involved in the biosynthesis of L-pipecolic acid and a DNA encoding a protein having the L-pipecolic acid cis-5-hydroxylase activity is cultured in a medium, and cis-5-hydroxy-L-pipecolic acid is collected from the medium.

15 Claims, 16 Drawing Sheets

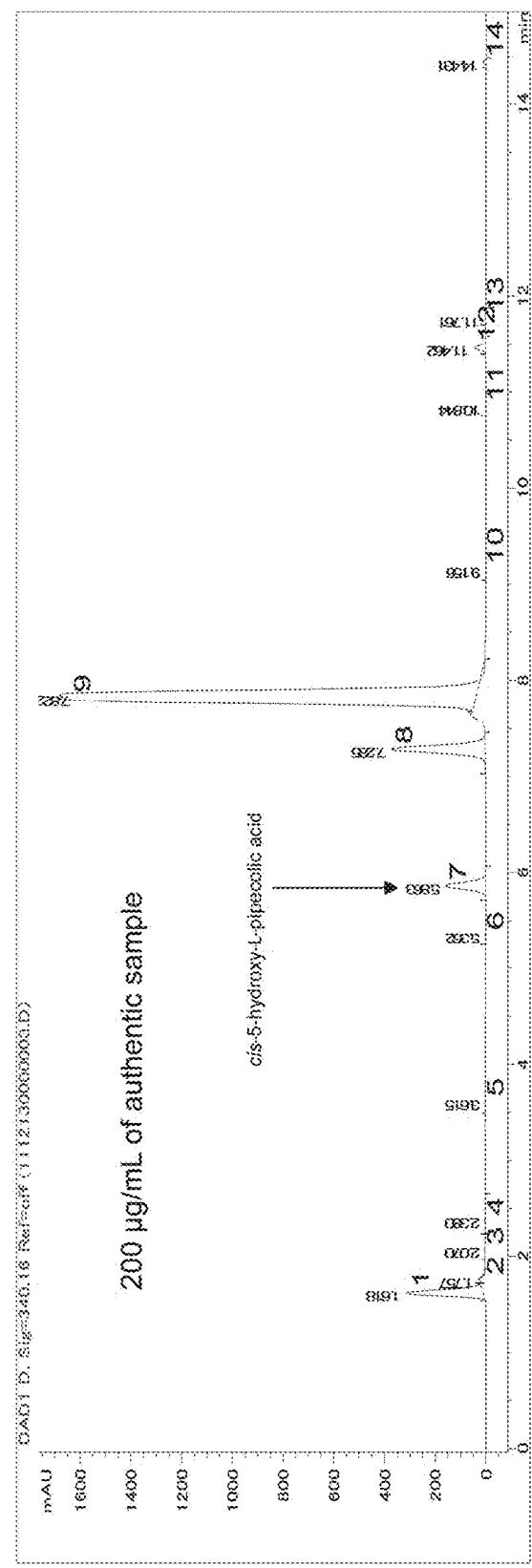

cis-5-hydroxy-L-pipecolic acid, 200 μg/mL of authentic sample

FIG. 5A lat sequence (SEQ ID Nos.: 1 and 22)

| | |
|---|---|
| atg tcc ctt ctt gcc ccg ctc gcc ccg ctc cgc gcc cat gcc ggc acc<br>Met Ser Leu Leu Ala Pro Leu Ala Pro Leu Arg Ala His Ala Gly Thr<br>1                 5                       10                15 | 48 |
| cgc ctt acc cag ggc ctg tct gac ccg cag gtc gag cag ctg gcc gcc<br>Arg Leu Thr Gln Gly Leu Ser Asp Pro Gln Val Glu Gln Leu Ala Ala<br>                20                   25                    30 | 96 |
| aac cac cct gac ctg cgc gcc gcc atc gac gcc gct gcc gac gaa tac<br>Asn His Pro Asp Leu Arg Ala Ala Ile Asp Ala Ala Ala Asp Glu Tyr<br>        35                       40                    45 | 144 |
| gcg cgc atc aaa ccg cag gcc gcg gca ttg ctg gac ctg gat gaa agc<br>Ala Arg Ile Lys Pro Gln Ala Ala Ala Leu Leu Asp Leu Asp Glu Ser<br>50                      55                       60 | 192 |
| gcg cag atc gcc gcc gtg cag gat ggc ttc gtc aac ttc tat gcc gat<br>Ala Gln Ile Ala Ala Val Gln Asp Gly Phe Val Asn Phe Tyr Ala Asp<br>65                      70                    75                80 | 240 |
| gat gcg gtg gtg ccc tat atc gcc ctg gcc gcc cgc ggg ccg tgg gtg<br>Asp Ala Val Val Pro Tyr Ile Ala Leu Ala Ala Arg Gly Pro Trp Val<br>                            85                       90                    95 | 288 |
| gtc agc ctg aag ggc gcg gtg ctg tat gac gcc ggc ggc tac ggc atg<br>Val Ser Leu Lys Gly Ala Val Leu Tyr Asp Ala Gly Gly Tyr Gly Met<br>                100                     105                  110 | 336 |
| ctc ggc ttc ggc cat acc ccg gcc gat atc ctg gag gcg gtc ggc aag<br>Leu Gly Phe Gly His Thr Pro Ala Asp Ile Leu Glu Ala Val Gly Lys<br>                115                     120                  125 | 384 |
| ccg cag gtg atg gcc aac atc atg act ccc tcg ctg gcc cag ggc cgc<br>Pro Gln Val Met Ala Asn Ile Met Thr Pro Ser Leu Ala Gln Gly Arg<br>                130                     135                  140 | 432 |
| ttc att gcc gca atg cgc cgc gaa atc ggc cat acc cgc ggc ggc tgc<br>Phe Ile Ala Ala Met Arg Arg Glu Ile Gly His Thr Arg Gly Gly Cys | 480 |

FIG. 5A (continued)

```
     145                      150                      155                      160
ccg  ttc  tcg  cac  ttc  atg  tgc  ctg  aac  tcc  ggc  tcc  gaa  gcg  gtc  ggg        528
Pro  Phe  Ser  His  Phe  Met  Cys  Leu  Asn  Ser  Gly  Ser  Glu  Ala  Val  Gly
                         165                      170                      175 ctg  gcc  gcg  cgc  atc  gcc  gac  atc  aac  gcc  aag  ctg  atg  acc  gac  ccg        576
Leu  Ala  Ala  Arg  Ile  Ala  Asp  Ile  Asn  Ala  Lys  Leu  Met  Thr  Asp  Pro
                         180                      185                      190 ggc  gcc  cgg  cat  gcc  ggc  gcc  acg  atc  aag  cgc  gtg  gtg  atc  aag  ggc        624
Gly  Ala  Arg  His  Ala  Gly  Ala  Thr  Ile  Lys  Arg  Val  Val  Ile  Lys  Gly
                         195                      200                      205 agt  ttc  cac  ggc  cgt  acc  gac  cgt  ccg  gcg  ctg  tat  tcc  gat  tcc  acc        672
Ser  Phe  His  Gly  Arg  Thr  Asp  Arg  Pro  Ala  Leu  Tyr  Ser  Asp  Ser  Thr
                         210                      215                      220 cgc  aag  gcc  tac  gat  gcg  cat  ctg  gcc  agc  tac  cgc  gac  gag  cac  agc        720
Arg  Lys  Ala  Tyr  Asp  Ala  His  Leu  Ala  Ser  Tyr  Arg  Asp  Glu  His  Ser
225                      230                      235                      240 gtc  att  gcc  atc  gcc  ccg  tat  gac  cag  cag  gcc  ctg  cgc  cag  gtg  ttt        768
Val  Ile  Ala  Ile  Ala  Pro  Tyr  Asp  Gln  Gln  Ala  Leu  Arg  Gln  Val  Phe
                         245                      250                      255 gcc  gat  gcc  cag  gcc  aac  cac  tgg  ttc  atc  gag  gcg  gtg  ttc  ctg  gag        816
Ala  Asp  Ala  Gln  Ala  Asn  His  Trp  Phe  Ile  Glu  Ala  Val  Phe  Leu  Glu
                         260                      265                      270 ccg  gtg  atg  ggc  gaa  ggc  gac  ccg  ggc  cgt  gcg  gtg  ccg  gtg  gac  ttc        864
Pro  Val  Met  Gly  Glu  Gly  Asp  Pro  Gly  Arg  Ala  Val  Pro  Val  Asp  Phe
                         275                      280                      285 tac  cgc  ctg  gcc  cgt  gag  ctg  acc  cgc  gaa  cac  ggc  agc  ctg  ctg  ctg        912
Tyr  Arg  Leu  Ala  Arg  Glu  Leu  Thr  Arg  Glu  His  Gly  Ser  Leu  Leu  Leu
                         290                      295                      300 atc  gat  tcg  atc  cag  gcc  gcg  ctg  cgc  gtg  cac  ggc  acc  ctg  tcc  ttc        960
Ile  Asp  Ser  Ile  Gln  Ala  Ala  Leu  Arg  Val  His  Gly  Thr  Leu  Ser  Phe
305                      310                      315                      320
```

FIG. 5A (continued)

```
gtc gac tac ccc ggc cac cag gag ctg gag gca ccg gac atg gag acc    1008
Val Asp Tyr Pro Gly His Gln Glu Leu Glu Ala Pro Asp Met Glu Thr
            325                 330                 335 tac tcc aag gcc ctg aac ggc gcc cag ttc ccg ctg tcg gta gtg gcc    1056
Tyr Ser Lys Ala Leu Asn Gly Ala Gln Phe Pro Leu Ser Val Val Ala
            340                 345                 350 gtg acc gag cac gcc gcc gcg ctg tac cgc aag ggc gtg tac ggc aac    1104
Val Thr Glu His Ala Ala Ala Leu Tyr Arg Lys Gly Val Tyr Gly Asn
            355                 360                 365 acc atg acc acc aac ccg cgg gcg ctg gac gtg gcc tgc gcc acc ctg    1152
Thr Met Thr Thr Asn Pro Arg Ala Leu Asp Val Ala Cys Ala Thr Leu
            370                 375                 380 gca cgc ctg gat gag ccg gtc cgc aac aat atc cgc ctg cgt ggc cag    1200
Ala Arg Leu Asp Glu Pro Val Arg Asn Asn Ile Arg Leu Arg Gly Gln
385                 390                 395                 400 cag gcg atg cag aag ctg gaa gca ttg aag gaa cgg ctg ggg ggc gcg    1248
Gln Ala Met Gln Lys Leu Glu Ala Leu Lys Glu Arg Leu Gly Gly Ala
            405                 410                 415 atc acc aag gtg cag ggc acc ggc ctg ctg ttc tcc tgc gag ctg gcc    1296
Ile Thr Lys Val Gln Gly Thr Gly Leu Leu Phe Ser Cys Glu Leu Ala
            420                 425                 430 ccg cag tac aag tgc tac ggg gcc ggc tcc acc gag gag tgg ctg cgc    1344
Pro Gln Tyr Lys Cys Tyr Gly Ala Gly Ser Thr Glu Glu Trp Leu Arg
            435                 440                 445 atg cac ggg gtc aat gtg atc cac ggc ggc gag aat tcg ctg cgc ttc    1392
Met His Gly Val Asn Val Ile His Gly Gly Glu Asn Ser Leu Arg Phe
            450                 455                 460 acc ccg cac ttc ggc atg gac gag gcc gaa ctg gac ctg ctg gtg gag    1440
Thr Pro His Phe Gly Met Asp Glu Ala Glu Leu Asp Leu Leu Val Glu
465                 470                 475                 480
```

FIG. 5A (continued)

| | |
|---|---|
| atg gtc ggg cgt gcg ctg gtc gaa ggc cca cgc cgg gcc tga<br>Met Val Gly Arg Ala Leu Val Glu Gly Pro Arg Arg Ala<br>485　　　　　　　　490 | 1482 |

FIG. 5B cis sequence (SEQ ID Nos.: 2 and 23)

| | |
|---|---|
| atg aag tca tac agt ctg ggg aag ttc gaa gac cgt agt att gac agt<br>Met Lys Ser Tyr Ser Leu Gly Lys Phe Glu Asp Arg Ser Ile Asp Ser<br>1　　　　　5　　　　　　10　　　　　　15 | 48 |
| ttg atc gaa gag gcc tcc ggc ctg ccc gac agc gcg tac agc tcg gcc<br>Leu Ile Glu Glu Ala Ser Gly Leu Pro Asp Ser Ala Tyr Ser Ser Ala<br>　　　　20　　　　　　25　　　　　　30 | 96 |
| tat caa gag tac tca atc ggc ctt tgg gac acg gcc acg cta tgg aat<br>Tyr Gln Glu Tyr Ser Ile Gly Leu Trp Asp Thr Ala Thr Leu Trp Asn<br>　　35　　　　　　40　　　　　　45 | 144 |
| gag cgc ggc aac gag tct ggt gaa gtc tca gag cac gcc gcg gcg gcg<br>Glu Arg Gly Asn Glu Ser Gly Glu Val Ser Glu His Ala Ala Ala Ala<br>50　　　　　　55　　　　　　60 | 192 |
| gcg cct acc gct atc ggc cga tcg acg cct cgg ctc aat gaa ttc gtg<br>Ala Pro Thr Ala Ile Gly Arg Ser Thr Pro Arg Leu Asn Glu Phe Val<br>65　　　　　　70　　　　　　75　　　　　　80 | 240 |
| cga gcg aaa ttc aat gtc gac gtt ttg cgc gct gtt cga cta ttt cgg<br>Arg Ala Lys Phe Asn Val Asp Val Leu Arg Ala Val Arg Leu Phe Arg<br>　　　　85　　　　　　90　　　　　　95 | 288 |
| gcg cgg caa ggc gcg atc atc att cct cat cgc gac tat ttg gag cac<br>Ala Arg Gln Gly Ala Ile Ile Ile Pro His Arg Asp Tyr Leu Glu His<br>　　　　100　　　　　　105　　　　　　110 | 336 |
| tcc aac ggg ttt tgc cgg atc cat ctt cct ttg gtg acg act ccg gga<br>Ser Asn Gly Phe Cys Arg Ile His Leu Pro Leu Val Thr Thr Pro Gly<br>　　　　115　　　　　　120　　　　　　125 | 384 |
| gcc cgt aat agc gag aat aac gag gtc tat cgc atg ttg cca ggc gag<br>Ala Arg Asn Ser Glu Asn Asn Glu Val Tyr Arg Met Leu Pro Gly Glu | 432 |

FIG. 5B (continued)

```
                130                     135                     140
        ctt  tgg  ttc  ctg  gac  agc  aac  gag  gtc  cat  tcg  ggt  gga  gtt  ctt  gat         480
        Leu  Trp  Phe  Leu  Asp  Ser  Asn  Glu  Val  His  Ser  Gly  Gly  Val  Leu  Asp
        145                      150                     155                     160 tcg  gga  act  cgg  atc  cat  tta  gtg  cta  gat  ttc  acc  cat  gag  cat  aac         528
        Ser  Gly  Thr  Arg  Ile  His  Leu  Val  Leu  Asp  Phe  Thr  His  Glu  His  Asn
                            165                     170                     175 gaa  aac  ccg  gct  gct  gtg  ttg  aaa  aac  gcg  gac  cga  tta  cgt  cct  att         576
        Glu  Asn  Pro  Ala  Ala  Val  Leu  Lys  Asn  Ala  Asp  Arg  Leu  Arg  Pro  Ile
                            180                     185                     190 gct  cgc  gat  ccg  cga  ata  tct  cga  tcc  aag  tta  gac  cac  gaa  gct  ctg         624
        Ala  Arg  Asp  Pro  Arg  Ile  Ser  Arg  Ser  Lys  Leu  Asp  His  Glu  Ala  Leu
                       195                     200                     205 gag  agc  ctg  atc  cga  ggc  ggt  cga  gtc  gtg  aca  ttg  gcg  atg  tgg  ccc         672
        Glu  Ser  Leu  Ile  Arg  Gly  Gly  Arg  Val  Val  Thr  Leu  Ala  Met  Trp  Pro
                  210                     215                     220 gcc  cta  gtg  cag  atg  ctc  gct  aga  atc  cat  ctg  aca  tct  gac  gcg  cat         720
        Ala  Leu  Val  Gln  Met  Leu  Ala  Arg  Ile  His  Leu  Thr  Ser  Asp  Ala  His
        225                     230                     235                     240 cct  gcc  gaa  ctt  tac  gac  tgg  ctg  gac  gat  ctt  gct  gac  cgc  agt  ggt         768
        Pro  Ala  Glu  Leu  Tyr  Asp  Trp  Leu  Asp  Asp  Leu  Ala  Asp  Arg  Ser  Gly
                            245                     250                     255 aac  gac  gag  ctt  gtg  gca  gag  gcg  cga  aga  atg  cgg  cga  tat  ttc  ttg         816
        Asn  Asp  Glu  Leu  Val  Ala  Glu  Ala  Arg  Arg  Met  Arg  Arg  Tyr  Phe  Leu
                            260                     265                     270 acg  gat  gga  ata  tcg  agg  act  cca  tcg  ttc  gag  cga  ttt  tgg  cgc  gag         864
        Thr  Asp  Gly  Ile  Ser  Arg  Thr  Pro  Ser  Phe  Glu  Arg  Phe  Trp  Arg  Glu
                       275                     280                     285 ctc  gat  gcg  gcg  cgg  aag  ggc  gag  cta  gtc  tcg  taa                              900
        Leu  Asp  Ala  Ala  Arg  Lys  Gly  Glu  Leu  Val  Ser
        290                     295
```

FIG. 5C mutant cis sequence (SEQ ID Nos.: 21 and 24)

| atg | aag | tca | tac | agt | ctg | ggg | aag | ttc | gaa | gac | cgt | agt | att | gac | agt | 48 |
|---|---|---|---|---|---|---|---|---|---|---|---|---|---|---|---|---|
| Met | Lys | Ser | Tyr | Ser | Leu | Gly | Lys | Phe | Glu | Asp | Arg | Ser | Ile | Asp | Ser | |
| 1 | | | | 5 | | | | | 10 | | | | | 15 | | |

| ttg | atc | gaa | gag | gcc | tcc | ggc | ctg | ccc | gac | agc | gcg | tac | agc | tcg | gcc | 96 |
|---|---|---|---|---|---|---|---|---|---|---|---|---|---|---|---|---|
| Leu | Ile | Glu | Glu | Ala | Ser | Gly | Leu | Pro | Asp | Ser | Ala | Tyr | Ser | Ser | Ala | |
| | | | 20 | | | | | 25 | | | | | 30 | | | |

| tat | caa | gag | tac | tca | atc | ggc | ctt | tgg | gac | acg | gcc | acg | cta | tgg | aat | 144 |
|---|---|---|---|---|---|---|---|---|---|---|---|---|---|---|---|---|
| Tyr | Gln | Glu | Tyr | Ser | Ile | Gly | Leu | Trp | Asp | Thr | Ala | Thr | Leu | Trp | Asn | |
| | | 35 | | | | | 40 | | | | | 45 | | | | |

| gag | cgc | ggt | aac | gag | tct | ggt | gaa | gtc | tca | gag | cac | gcc | gcg | gcg | gcg | 192 |
|---|---|---|---|---|---|---|---|---|---|---|---|---|---|---|---|---|
| Glu | Arg | Gly | Asn | Glu | Ser | Gly | Glu | Val | Ser | Glu | His | Ala | Ala | Ala | Ala | |
| | 50 | | | | | 55 | | | | | 60 | | | | | |

| gcg | cct | acc | gct | atc | ggc | cga | tcg | acg | cct | cgg | ctc | aat | gaa | ttc | gtg | 240 |
|---|---|---|---|---|---|---|---|---|---|---|---|---|---|---|---|---|
| Ala | Pro | Thr | Ala | Ile | Gly | Arg | Ser | Thr | Pro | Arg | Leu | Asn | Glu | Phe | Val | |
| 65 | | | | | 70 | | | | | 75 | | | | | 80 | |

| cga | gcg | aaa | ttc | aat | gtc | gac | gtt | ttg | cgc | gct | gtt | cga | cta | ttt | cgg | 288 |
|---|---|---|---|---|---|---|---|---|---|---|---|---|---|---|---|---|
| Arg | Ala | Lys | Phe | Asn | Val | Asp | Val | Leu | Arg | Ala | Val | Arg | Leu | Phe | Arg | |
| | | | | 85 | | | | | 90 | | | | | 95 | | |

| gcg | cgg | caa | ggc | gcg | atc | atc | att | cct | cat | cgc | gac | tat | ttg | gag | cac | 336 |
|---|---|---|---|---|---|---|---|---|---|---|---|---|---|---|---|---|
| Ala | Arg | Gln | Gly | Ala | Ile | Ile | Ile | Pro | His | Arg | Asp | Tyr | Leu | Glu | His | |
| | | | 100 | | | | | 105 | | | | | 110 | | | |

| tcc | aac | ggg | ttt | tgc | cgg | atc | cat | ctt | cct | ttg | gtg | acg | act | ccg | gga | 384 |
|---|---|---|---|---|---|---|---|---|---|---|---|---|---|---|---|---|
| Ser | Asn | Gly | Phe | Cys | Arg | Ile | His | Leu | Pro | Leu | Val | Thr | Thr | Pro | Gly | |
| | | 115 | | | | | 120 | | | | | 125 | | | | |

| gcc | cgt | aat | agc | gag | aat | aac | gag | gtc | tat | cgc | atg | atg | cca | ggc | gag | 432 |
|---|---|---|---|---|---|---|---|---|---|---|---|---|---|---|---|---|
| Ala | Arg | Asn | Ser | Glu | Asn | Asn | Glu | Val | Tyr | Arg | Met | Met | Pro | Gly | Glu | |
| | | 130 | | | | | 135 | | | | | 140 | | | | |

FIG. 5C (continued)

```
ctt tgg ttc ctg gac agc aac gag gtc cat tcg ggt gga gtt ctt gat     480
Leu Trp Phe Leu Asp Ser Asn Glu Val His Ser Gly Gly Val Leu Asp
145             150                 155                 160 tcg gga act cgg atc cat tta gtg cta gat ttc acc cat gag cat aac     528
Ser Gly Thr Arg Ile His Leu Val Leu Asp Phe Thr His Glu His Asn
            165                 170                 175 gaa aac ccg gct gct gtg ttg aaa aac gcg gac cga tta cgt cct att     576
Glu Asn Pro Ala Ala Val Leu Lys Asn Ala Asp Arg Leu Arg Pro Ile
                180                 185                 190 gct cgc gat ccg cga ata tct cga tcc aag tta gac cac gaa gct ctg     624
Ala Arg Asp Pro Arg Ile Ser Arg Ser Lys Leu Asp His Glu Ala Leu
            195                 200                 205 gag agc ctg atc cga ggc ggt cga gtc gtg aca ttg gcg atg tgg ccc     672
Glu Ser Leu Ile Arg Gly Gly Arg Val Val Thr Leu Ala Met Trp Pro
210                 215                 220 gcc cta gtg cag atg ctc gct aga atc cat ctg aca tct gac gcg cat     720
Ala Leu Val Gln Met Leu Ala Arg Ile His Leu Thr Ser Asp Ala His
225                 230                 235                 240 cct gcc gaa ctt tac gac tgg ctg gac gat ctt gct gac cgc agt ggt     768
Pro Ala Glu Leu Tyr Asp Trp Leu Asp Asp Leu Ala Asp Arg Ser Gly
            245                 250                 255 aac gac gag ctt gtg gca gag gcg cga aga atg cgg cga tat ttc ttg     816
Asn Asp Glu Leu Val Ala Glu Ala Arg Arg Met Arg Arg Tyr Phe Leu
                260                 265                 270 acg gat gga ata tcg agg act cca tcg ttc gag cga ttt tgg cgc gag     864
Thr Asp Gly Ile Ser Arg Thr Pro Ser Phe Glu Arg Phe Trp Arg Glu
            275                 280                 285 ctc gat gcg gcg cgg aag ggc gag cta gtc tcg taa                      900
Leu Asp Ala Ala Arg Lys Gly Glu Leu Val Ser
290                 295
``` a size of 26 KB. The

SEQUENCE LISTING

<160> NUMBER OF SEQ ID NOS: 30

<210> SEQ ID NO 1
<211> LENGTH: 1482
<212> TYPE: DNA
<213> ORGANISM: Flavobacterium lutescens IFO3084

<400> SEQUENCE: 1

```
atgtccctte ttgccccgct cgccccgctc cgcgcccatg ccggcacccg ccttacccag      60
ggcctgtctg acccgcaggt cgagcagctg gccgccaacc accctgacct gcgcgccgcc     120
atcgacgccg ctgccgacga atacgcgcgc atcaaaccgc aggccgcggc attgctggac     180
ctggatgaaa gcgcgcagat cgccgccgtg caggatggct tcgtcaactt ctatgccgat     240
gatgcggtgg tgccctatat cgccctggcc gcccgcgggc cgtgggtggt cagcctgaag     300
ggcgcggtgc tgtatgacgc cggcggctac ggcatgctcg gcttcggcca taccccggcc     360
gatatcctgg aggcggtcgg caagccgcag gtgatggcca acatcatgac tccctcgctg     420
gcccagggcc gcttcattgc cgcaatgcgc cgcgaaatcg ccataccccg cggcggctgc     480
ccgttctcgc acttcatgtg cctgaactcc ggctccgaag cggtcgggct ggccgcgcgc     540
atcgccgaca tcaacgccaa gctgatgacc gacccgggcg cccggcatgc cggcgccacg     600
atcaagcgcg tggtgatcaa gggcagtttc cacggccgta ccgaccgtcc ggcgctgtat     660
```

```
tccgattcca cccgcaaggc ctacgatgcg catctggcca gctaccgcga cgagcacagc      720
gtcattgcca tcgccccgta tgaccagcag gccctgcgcc aggtgtttgc cgatgcccag      780
gccaaccact ggttcatcga ggcggtgttc ctggagccgg tgatgggcga aggcgacccg      840
ggccgtgcgg tgccggtgga cttctaccgc ctggcccgtg agctgacccg cgaacacggc      900
agcctgctgc tgatcgattc gatccaggcc gcgctgcgcg tgcacggcac cctgtccttc      960
gtcgactacc ccggccacca ggagctggag gcaccggaca tggagaccta ctccaaggcc     1020
ctgaacggcg cccagttccc gctgtcggta gtggccgtga ccgagcacgc cgccgcgctg     1080
taccgcaagg gcgtgtacgg caacaccatg accaccaacc gcggcgcgct ggacgtggcc     1140
tgcgccaccc tggcacgcct ggatgagccg gtccgcaaca atatccgcct gcgtggccag     1200
caggcgatgc agaagctgga agcattgaag gaacggctgg ggggcgcgat caccaaggtg     1260
cagggcaccg gcctgctgtt ctcctgcgag ctggccccgc agtacaagtg ctacggggcc     1320
ggctccaccg aggagtggct cgcatgcac ggggtcaatg tgatccacgg cggcgagaat     1380
tcgctgcgct tcaccccgca cttcggcatg gacgaggcca actgacctt gctggtggag     1440
atggtcgggc gtgcgctggt cgaaggccca cgccgggcct ga                       1482

<210> SEQ ID NO 2
<211> LENGTH: 900
<212> TYPE: DNA
<213> ORGANISM: Segniliparus rugosus  ATCC BAA-974

<400> SEQUENCE: 2
atgaagtcat acagtctggg gaagttcgaa gaccgtagta ttgacagttt gatcgaagag       60
gcctccggcc tgcccgacag cgcgtacagc tcggcctatc aagagtactc aatcggcctt      120
tgggacacgg ccacgctatg gaatgagcgc ggcaacgagt ctggtgaagt ctcagagcac      180
gccgcggcgg cggcgcctac cgctatcggc cgatcgacgc ctcggctcaa tgaattcgtg      240
cgagcgaaat tcaatgtcga cgttttgcgc gctgttcgac tatttcgggc gcggcaaggc      300
gcgatcatca ttcctcatcg cgactatttg gagcactcca acgggttttg ccggatccat      360
cttcctttgg tgacgactcc gggagcccgt aatagcgaga ataacgaggt ctatcgcatg      420
ttgccaggcg agctttggtt cctggacagc aacgaggtcc attcgggtgg agttcttgat      480
tcgggaactc ggatccattt agtgctagat tcacccatg agcataacga aaacccggct      540
gctgtgttga aaaacgcgga ccgattacgt cctattgctc gcgatccgcg aatatctcga      600
tccaagttag accacgaagc tctggagagc ctgatccgag gcggtcgagt cgtgacattg      660
gcgatgtggc ccgccctagt gcagatgctc gctagaatcc atctgacatc tgacgcgcat      720
cctgccgaac tttacgactg gctggacgat cttgctgacc gcagtggtaa cgacgagctt      780
gtggcagagg cgcgaagaat gcggcgatat ttcttgacgg atggaatatc gaggactcca      840
tcgttcgagc gattttggcg cgagctcgat gcggcgcgga agggcgagct agtctcgtaa      900

<210> SEQ ID NO 3
<211> LENGTH: 810
<212> TYPE: DNA
<213> ORGANISM: Escherichia coli

<400> SEQUENCE: 3
atggaaaaga aaatcggttt tattggctgc ggcaatatgg aaaagccat tctcggcggt       60
ctgattgcca gcggtcaggt gcttccaggg caaatctggg tatacacccc ctcccggat      120
aaagtcgccg ccctgcatga ccagttcggc atcaacgccg cagaatcggc gcaagaagtg      180
```

-continued

| | |
|---|---|
| gcgcaaatcg ccgacatcat ttttgctgcc gttaaacctg gcatcatgat taaagtgctt | 240 |
| agcgaaatca cctccagcct gaataaagac tctctggtcg tttctattgc tgcaggtgtc | 300 |
| acgctcgacc agcttgcccg cgcgctgggc catgaccgga aaattatccg cgccatgccg | 360 |
| aacactcccg cactggttaa tgccgggatg acctccgtaa cgccaaacgc gctggtaacc | 420 |
| ccagaagata ccgctgatgt gctgaatatt ttccgctgct ttggcgaagc ggaagtaatt | 480 |
| gctgagccga tgatccaccc ggtggtcggt gtgagcggtt cttcgccagc ctacgtattt | 540 |
| atgtttatcg aagcgatggc cgacgccgcc gtgctgggcg ggatgccacg cgcccaggcg | 600 |
| tataaatttg ccgctcaggc ggtaatgggt tccgcaaaaa tggtgctgga acgggagaa | 660 |
| catccggggg cactgaaaga tatggtctgc tcaccgggag gcaccaccat tgaagcggta | 720 |
| cgcgtactgg aagagaaagg cttccgtgct gcagtgatcg aagcgatgac gaagtgtatg | 780 |
| gaaaaatcag aaaaactcag caaatcctga | 810 |

<210> SEQ ID NO 4
<211> LENGTH: 1470
<212> TYPE: DNA
<213> ORGANISM: Escherichia coli

<400> SEQUENCE: 4

| | |
|---|---|
| atggtttccg aaactaaaac cacagaagcg ccgggcttac gccgtgaatt aaaggcgcgt | 60 |
| cacctgacga tgattgccat ggcggttcc atcggtacag gtcttttgt tgcctctggc | 120 |
| gcaacgattt ctcaggcagg tccgggcggg gcattgctct cgtatatgct gattggcctg | 180 |
| atggtttact tcctgatgac cagtctcggt gaactggctg catatatgcc ggtttccggt | 240 |
| tcgtttgcca cttacggtca gaactatgtt gaagaaggct ttggcttcgc gctgggctgg | 300 |
| aactactggt acaactgggc ggtgactatc gccgttgacc tggttgcagc tcagctggtc | 360 |
| atgagctggt ggttcccgga taccgggc tggatctgga gtgcgttgtt cctcggcgtt | 420 |
| atcttcctgc tgaactacat ctcagttcgt ggctttggtg aagcggaata ctggttctca | 480 |
| ctgatcaaag tcacgacagt tattgtcttt atcatcgttg gcgtgctgat gattatcggt | 540 |
| atcttcaaag gcgcgcagcc tgcgggctgg agcaactgga caatcggcga agcgccgttt | 600 |
| gctggtggtt ttgcggcgat gatcggcgta gctatgattg tcggcttctc tttccaggga | 660 |
| accgagctga tcgtattgc tgcaggcgag tccgaagatc cggcgaaaaa cattccacgc | 720 |
| gcggtacgtc aggtgttctg gcgaatcctg ttgttctatg tgttcgcgat cctgattatc | 780 |
| agcctgatta ttccgtacac cgatccgagc ctgctgcgta cgatgttaa agacatcagc | 840 |
| gttagtccgt tcacccctggt gttccagcac gcgggtctgc tctctgcggc ggcggtgatg | 900 |
| aacgcagtta ttctgacggc ggtgctgtca gcgggtaact ccggtatgta tgcgtctact | 960 |
| cgtatgctgt acaccctggc cgtgtgacggt aaagcgccgc gcattttcgc taaactgtcg | 1020 |
| cgtggtggcg tgccgcgtaa tgcgctgtat gcgacgacgg tgattgccgg tctgtgcttc | 1080 |
| ctgacctcca tgtttggcaa ccagacggta tacctgtggc tgctgaacac ctccgggatg | 1140 |
| acgggtttta tcgcctggct ggggattgcc attagccact atcgcttccg tcgcggttac | 1200 |
| gtattgcagg acacgacat taacgatctg ccgtaccgtt caggtttctt cccactgggg | 1260 |
| ccgatcttcg cattcattct gtgtctgatt atcactttgg gccagaacta cgaagcgttc | 1320 |
| ctgaaagata ctattgactg gggcggcgta gcggcaacgt atattggtat cccgctgttc | 1380 |
| ctgattattt ggttcggcta caagctgatt aaaggaactc acttcgtacg ctacagcgaa | 1440 |

```
atgaagttcc cgcagaacga taagaaataa                                      1470
```

<210> SEQ ID NO 5
<211> LENGTH: 1275
<212> TYPE: DNA
<213> ORGANISM: Bacillus subtilis subsp. subtilis str. 168

<400> SEQUENCE: 5

```
atgtcagcaa agcaagtctc gaaagatgaa gaaaaagaag ctcttaactt atttctgtct     60
acccaaacaa tcattaagga agcccttcgg aagctgggtt atccgggaga tatgtatgaa    120
ctcatgaaag agccgcagag aatgctcact gtccgcattc cggtcaaaat ggacaatggg    180
agcgtcaaag tgttcacagg ctaccggtca cagcacaatg atgctgtcgg tccgacaaag    240
gggggcgttc gcttccatcc agaagttaat gaagaggaag taaaggcatt atccatttgg    300
atgacgctca aatgcgggat tgccaatctt ccttacggcg gcgggaaggg cggtattatt    360
tgtgatccgc ggacaatgtc atttggagaa ctggaaaggc tgagcagggg gtatgtccgt    420
gccatcagcc agatcgtcgg tccgacaaag gatattccag ctcccgatgt gtacaccaat    480
tcgcagatta tggcgtggat gatggatgag tacagccggc tgcgggaatt cgattctccg    540
ggctttatta caggtaaacc gcttgttttg ggaggatcgc aaggacggga aacagcgacg    600
gcacagggcg tcacgatttg tattgaagag gcggtgaaga aaaagggat caagctgcaa    660
aacgcgcgca tcatcataca gggctttgga aacgcgggta gcttcctggc caaattcatg    720
cacgatgcgg gcgcgaaggt gatcgggatt tctgatgcca atggcgggct ctacaaccca    780
gacggccttg atatcccttta tttgctcgat aaacgggaca gctttggtat ggtcaccaat    840
ttatttactg acgtcatcac aaatgaggag ctgcttgaaa aggattgcga tattttagtg    900
cctgccgcga tctccaatca aatcacagcc aaaaacgcac ataacattca ggcgtcaatc    960
gtcgttgaac gggcgaacgg cccgacaacc attgatgcca ctaagatcct gaatgaaaga   1020
ggcgtgctgc ttgtgccgga tatcctagcg agtgccggcg gcgtcacggt ttcttatttt   1080
gaatgggtgc aaaacaacca aggatattat tggtcggaag aagaggttgc agaaaaactg   1140
agaagcgtca tggtcagctc gttcgaaaca atttatcaaa cagcggcaac acataaagtg   1200
gatatgcgtt tggcggctta catgacgggc atcagaaaat cggcagaagc atcgcgtttc   1260
cgcggatggg tctaa                                                    1275
```

<210> SEQ ID NO 6
<211> LENGTH: 843
<212> TYPE: DNA
<213> ORGANISM: Sinorhizobium meliloti 1021

<400> SEQUENCE: 6

```
atgagcaccc atttcttggg caaggtcaag ttcgatgaag cgcgattggc agaagatcta     60
tctaccttgg aagttgccga gttctcgagt gcatactcgg acttcgcgtg cggtaaatgg    120
gaggcatgcg tgctacgcaa tcggaccgga atgcaggagg aagatatcgt cgtaagtcac    180
aacgctcctg cactggccac gccgctgagc aagtcgctgc cgtatctgaa cgaacttgtt    240
gaaacccact tcgattgcag cgctgttcgg tatacaagaa ttgtccgtgt atcagaaaac    300
gcatgtataa tcccccatag tgattaccta gaactagatg agaccttcac aaggttacac    360
ctggtgttag acactaattc aggatgcgct aatactgagg aagataaaat atttcatatg    420
ggactgggag agatttggtt ccttgacgct atgttaccgc atagcgctgc ttgttttcc    480
aaaactccgc gcctgcatct gatgatcgac tttgaggcta ccgcttttcc cgaatctttt    540
```

```
ctgcgaaatg tcgaacaacc agtgacaaca cgagacatgg ttgatcctcg gaaggaacta    600
accgatgagg ttatcgaagg tattctgggg ttttcaataa ttattagcga agccaattac    660
cgggaaattg tttctattct ggcgaagcta cacttcttct acaaggcaga ctgtcgatca    720
atgtacgact ggctgaagga aatctgcaaa cgtcgagggg atcctgcact tattgaaaag    780
accgcctcgc tcgagcgatt ttttctaggg caccgtgaac gtggcgaggt gatgacatac    840
taa                                                                 843

<210> SEQ ID NO 7
<211> LENGTH: 843
<212> TYPE: DNA
<213> ORGANISM: Mesorhizobium loti MAFF303099

<400> SEQUENCE: 7
atgacaacgc ggatattggg tgtggtccag cttgatcaaa ggcgactgac agacgatttg     60
gctgtcttag cgaagtccaa cttctcgagc gaatattcgg atttcgcctg cgggcggtgg    120
gaattctgca tgctccgcaa tcagtcgggg aagcaggagg agcagagagt ggtcgtccac    180
gagaccccag cgctggcgac acctctgggc caatccttac cctatctcaa tgaattgttg    240
gacaatcact tgataggga ctctatacgc tacgcgcgga tcatccggat atcagaaaac     300
gcgtgtataa tacctcaccg tgattacttg gaactagaag ggaaatttat cagagtgcac    360
ctagttctag atacgaatga aaagtgttcc aatacagaag agaataatat attccatatg    420
ggacgaggtg agatctggtt tcttgacgca agcctgccgc acagcgcggg atgtttctca    480
ccaactccac gcttacatct agtggtcgac atcgagggga ctcgttccct ggaagaggtt    540
gcaatcaatg tcgaacagcc gtcggcaagg aatgccacgg tggatactcg caaggagtgg    600
actgatgaaa cgctcgaatc cgttctggga ttttcggaga ttatcagcga ggccaattat    660
cgagagatcg tcgcgattct ggcgaagctc cactttttcc acaaggtcca ctgcgtggat    720
atgtatggct ggcttaagga aatctgccga cgtcgtggcg agccggcgct tatagaaaag    780
gccaactcgc ttgagcgatt ttatctcatt gaccgtgctg ctggcgaggt catgacttat    840
tga                                                                 843

<210> SEQ ID NO 8
<211> LENGTH: 852
<212> TYPE: DNA
<213> ORGANISM: Segniliparus rugosus ATCC BAA-974

<400> SEQUENCE: 8
ttgatcgaag aggcctccgg cctgcccgac agcgcgtaca gctcggccta tcaagagtac     60
tcaatcggcc tttgggacac ggccacgcta tggaatgagc gcggcaacga gtctggtgaa    120
gtctcagagc acgccgcggc ggcggcgcct accgctatcg ccgatcgac gcctcggctc     180 aatgaattcg tgcgagcgaa attcaatgtc gacgttttgc gcgctgttcg actatttcgg    240
gcgcggcaag gcgcgatcat cattcctcat cgcgactatt ggagcactc caacgggttt    300 tgccggatcc atcttccttt ggtgacgact ccgggagccc gtaatagcga gaataacgag    360
gtctatcgca tgttgccagg cgagcttgg ttcctggaca gcaacgaggt ccattcgggt    420
ggagttcttg attcgggaac tcggatccat ttagtgctag atttcaccca tgagcataac    480
gaaaacccgg ctgctgtgtt gaaaaacgcg gaccgattac gtcctattgc tcgcgatccg    540
cgaatatctc gatccaagtt agaccacgaa gctctggaga gcctgatccg aggcggtcga    600
```

-continued

```
gtcgtgacat tggcgatgtg gcccgcccta gtgcagatgc tcgctagaat ccatctgaca      660
tctgacgcgc atcctgccga actttacgac tggctggacg atcttgctga ccgcagtggt      720
aacgacgagc ttgtggcaga ggcgcgaaga atgcggcgat atttcttgac ggatggaata      780
tcgaggactc catcgttcga gcgatttttgg cgcgagctcg atgcggcgcg aagggcgag       840 ctagtctcgt aa                                                          852

<210> SEQ ID NO 9
<211> LENGTH: 41
<212> TYPE: DNA
<213> ORGANISM: Artificial Sequence
<220> FEATURE:
<223> OTHER INFORMATION: Primer lac-lat-NcoF2

<400> SEQUENCE: 9
aaaccatggc catgattacg ccaagcttgt cccttcttgc c                           41

<210> SEQ ID NO 10
<211> LENGTH: 34
<212> TYPE: DNA
<213> ORGANISM: Artificial Sequence
<220> FEATURE:
<223> OTHER INFORMATION: Primer lat-XhoR

<400> SEQUENCE: 10
gggctcgagt caggcccggc gtgggccttc gacc                                   34

<210> SEQ ID NO 11
<211> LENGTH: 50
<212> TYPE: DNA
<213> ORGANISM: Artificial Sequence
<220> FEATURE:
<223> OTHER INFORMATION: Primer lysP-SD-XhoF

<400> SEQUENCE: 11
gggctcgaga agaaggagat atagatatgg tttccgaaac taaaaccaca                  50

<210> SEQ ID NO 12
<211> LENGTH: 33
<212> TYPE: DNA
<213> ORGANISM: Artificial Sequence
<220> FEATURE:
<223> OTHER INFORMATION: Primer lysP-KpnR

<400> SEQUENCE: 12
cccggtacct tatttcttat cgttctgcgg gaa                                    33

<210> SEQ ID NO 13
<211> LENGTH: 51
<212> TYPE: DNA
<213> ORGANISM: Artificial Sequence
<220> FEATURE:
<223> OTHER INFORMATION: Primer proC-SD-KpnF

<400> SEQUENCE: 13
gggggtacca agaaggagat atagatatgg aaaagaaaat cggttttatt g                51

<210> SEQ ID NO 14
<211> LENGTH: 32
<212> TYPE: DNA
<213> ORGANISM: Artificial Sequence
<220> FEATURE:
<223> OTHER INFORMATION: Primer proC-BamR

<400> SEQUENCE: 14
```

```
cccggatcct caggatttgc tgagtttttc tg                                    32
```

<210> SEQ ID NO 15
<211> LENGTH: 50
<212> TYPE: DNA
<213> ORGANISM: Artificial Sequence
<220> FEATURE:
<223> OTHER INFORMATION: Primer rocG-SD-BamF

<400> SEQUENCE: 15

```
cttggatcca gaaggagata tagatatgtc agcaaagcaa gtctcgaaag                 50
```

<210> SEQ ID NO 16
<211> LENGTH: 33
<212> TYPE: DNA
<213> ORGANISM: Artificial Sequence
<220> FEATURE:
<223> OTHER INFORMATION: Primer rocG-XbaR

<400> SEQUENCE: 16

```
cttaagcttt tagacccatc cgcggaaacg cga                                   33
```

<210> SEQ ID NO 17
<211> LENGTH: 35
<212> TYPE: DNA
<213> ORGANISM: Artificial Sequence
<220> FEATURE:
<223> OTHER INFORMATION: Primer segni-short-NdeF

<400> SEQUENCE: 17

```
aaacatatga tcgaagaggc ctccggcctg cccga                                 35
```

<210> SEQ ID NO 18
<211> LENGTH: 41
<212> TYPE: DNA
<213> ORGANISM: Artificial Sequence
<220> FEATURE:
<223> OTHER INFORMATION: Primer segni-cis-BglR

<400> SEQUENCE: 18

```
gggagatctt tacgagacta gctcgccctt ccgcgccgca t                          41
```

<210> SEQ ID NO 19
<211> LENGTH: 35
<212> TYPE: DNA
<213> ORGANISM: Artificial Sequence
<220> FEATURE:
<223> OTHER INFORMATION: Primer segni-cis-NdeF2

<400> SEQUENCE: 19

```
aaacatatga tcgaagaggc ctccggcctg cccga                                 35
```

<210> SEQ ID NO 20
<211> LENGTH: 40
<212> TYPE: DNA
<213> ORGANISM: Artificial Sequence
<220> FEATURE:
<223> OTHER INFORMATION: Primer lat-(Spe)AflR2

<400> SEQUENCE: 20

```
gggcttaagc ttaagtcagg cccggcgtgg gccttcgacc                            40
```

<210> SEQ ID NO 21
<211> LENGTH: 53
<212> TYPE: DNA

<210> SEQ ID NO 21
<211> LENGTH: 53
<212> TYPE: DNA
<213> ORGANISM: Artificial Sequence
<220> FEATURE:
<223> OTHER INFORMATION: Primer loti-SD-pacF

<400> SEQUENCE: 21
cccttaatta agaaggaga tatacacatg acaacgcgga tattgggtgt ggt    53

<210> SEQ ID NO 22
<211> LENGTH: 37
<212> TYPE: DNA
<213> ORGANISM: Artificial Sequence
<220> FEATURE:
<223> OTHER INFORMATION: Primer loti-AvrR

<400> SEQUENCE: 22
aaacctaggt caataagtca tgacctcgcc agcagca    37

<210> SEQ ID NO 23
<211> LENGTH: 900
<212> TYPE: DNA
<213> ORGANISM: Artificial Sequence
<220> FEATURE:
<223> OTHER INFORMATION: Mutant-type cis

<400> SEQUENCE: 23

| atg aag tca tac agt ctg ggg aag ttc gaa gac cgt agt att gac agt | 48 |
|---|---|
| ttg atc gaa gag gcc tcc ggc ctg ccc gac agc gcg tac agc tcg gcc | 96 |
| tat caa gag tac tca atc ggc ctt tgg gac acg gcc acg cta tgg aat | 144 |
| gag cgc ggt aac gag tct ggt gaa gtc tca gag cac gcc gcg gcg gcg | 192 |
| gcg cct acc gct atc ggc cga tcg acg cct cgg ctc aat gaa ttc gtg | 240 |
| cga gcg aaa ttc aat gtc gac gtt ttt gcg gct gtt cga cta ttt cgg | 288 |
| gcg cgg caa ggc gcg atc atc att cct cat cgc gac tat ttg gag cac | 336 |
| tcc aac ggg ttt tgc cgg atc cat ctt cct ttg gtg acg act ccg gga | 384 |
| gcc cgt aat agc gag aat aac gag gtc tat cgc atg atg cca ggc gag | 432 |
| ctt tgg ttc ctg gac agc aac gag gtc cat tcg ggt gga gtt ctt gat | 480 |
| tcg gga act cgg atc cat tta gtg cta gat ttc acc cat gag cat aac | 528 |
| gaa aac ccg gct gct gtg ttg aaa aac gcg gac cga tta cgt cct att | 576 |
| gct cgc gat ccg cga ata tct cga tcc aag tta gac cac gaa gct ctg | 624 |
| gag agc ctg atc cga ggc ggt cga gtc gtg aca ttg gcg atg tgg ccc | 672 |
| gcc cta gtg cag atg ctc gct aga atc cat ctg aca tct gac gcg cat | 720 |
| cct gcc gaa ctt tac gac tgg ctg gac gat ctt gct gac cgc agt ggt | 768 |
| aac gac gag ctt gtg gca gag gcg cga aga atg cgg cga tat ttc ttg | 816 |
| acg gat gga ata tcg agg act cca tcg ttc gag cga ttt tgg cgc gag | 864 |
| ctc gat gcg gcg cgg aag ggc gag cta gtc tcg taa | 900 |

<210> SEQ ID NO 24
<211> LENGTH: 493
<212> TYPE: PRT
<213> ORGANISM: Flavobacterium lutescens IFO3084

<400> SEQUENCE: 24

Met Ser Leu Leu Ala Pro Leu Ala Pro Leu Arg Ala His Ala Gly Thr
1               5                   10                  15

```
Arg Leu Thr Gln Gly Leu Ser Asp Pro Gln Val Glu Gln Leu Ala Ala
            20                  25                  30

Asn His Pro Asp Leu Arg Ala Ala Ile Asp Ala Ala Asp Glu Tyr
        35                  40                  45

Ala Arg Ile Lys Pro Gln Ala Ala Leu Leu Asp Leu Asp Glu Ser
 50                  55                  60

Ala Gln Ile Ala Ala Val Gln Asp Gly Phe Val Asn Phe Tyr Ala Asp
 65                  70                  75                  80

Asp Ala Val Val Pro Tyr Ile Ala Leu Ala Ala Arg Gly Pro Trp Val
                85                  90                  95

Val Ser Leu Lys Gly Ala Val Leu Tyr Asp Ala Gly Tyr Gly Met
            100                 105                 110

Leu Gly Phe Gly His Thr Pro Ala Asp Ile Leu Glu Ala Val Gly Lys
            115                 120                 125

Pro Gln Val Met Ala Asn Ile Met Thr Pro Ser Leu Ala Gln Gly Arg
            130                 135                 140

Phe Ile Ala Ala Met Arg Arg Glu Ile Gly His Thr Arg Gly Gly Cys
145                 150                 155                 160

Pro Phe Ser His Phe Met Cys Leu Asn Ser Gly Ser Glu Ala Val Gly
                165                 170                 175

Leu Ala Ala Arg Ile Ala Asp Ile Asn Ala Lys Leu Met Thr Asp Pro
                180                 185                 190

Gly Ala Arg His Ala Gly Ala Thr Ile Lys Arg Val Val Ile Lys Gly
                195                 200                 205

Ser Phe His Gly Arg Thr Asp Arg Pro Ala Leu Tyr Ser Asp Ser Thr
210                 215                 220

Arg Lys Ala Tyr Asp Ala His Leu Ala Ser Tyr Arg Asp Glu His Ser
225                 230                 235                 240

Val Ile Ala Ile Ala Pro Tyr Asp Gln Gln Ala Leu Arg Gln Val Phe
                245                 250                 255

Ala Asp Ala Gln Ala Asn His Trp Phe Ile Glu Ala Val Phe Leu Glu
                260                 265                 270

Pro Val Met Gly Glu Gly Asp Pro Gly Arg Ala Val Pro Val Asp Phe
            275                 280                 285

Tyr Arg Leu Ala Arg Glu Leu Thr Arg Glu His Gly Ser Leu Leu Leu
290                 295                 300

Ile Asp Ser Ile Gln Ala Ala Leu Arg Val His Gly Thr Leu Ser Phe
305                 310                 315                 320

Val Asp Tyr Pro Gly His Gln Glu Leu Glu Ala Pro Asp Met Glu Thr
                325                 330                 335

Tyr Ser Lys Ala Leu Asn Gly Ala Gln Phe Pro Leu Ser Val Val Ala
            340                 345                 350

Val Thr Glu His Ala Ala Leu Tyr Arg Lys Gly Val Tyr Gly Asn
            355                 360                 365

Thr Met Thr Thr Asn Pro Arg Ala Leu Asp Val Ala Cys Ala Thr Leu
        370                 375                 380

Ala Arg Leu Asp Glu Pro Val Arg Asn Asn Ile Arg Leu Arg Gly Gln
385                 390                 395                 400

Gln Ala Met Gln Lys Leu Glu Ala Leu Lys Glu Arg Leu Gly Gly Ala
                405                 410                 415

Ile Thr Lys Val Gln Gly Thr Gly Leu Leu Phe Ser Cys Glu Leu Ala
            420                 425                 430

Pro Gln Tyr Lys Cys Tyr Gly Ala Gly Ser Thr Glu Glu Trp Leu Arg
```

```
            435                 440                 445
Met His Gly Val Asn Val Ile His Gly Gly Glu Asn Ser Leu Arg Phe
        450                 455                 460

Thr Pro His Phe Gly Met Asp Glu Ala Glu Leu Asp Leu Leu Val Glu
465                 470                 475                 480

Met Val Gly Arg Ala Leu Val Glu Gly Pro Arg Arg Ala
                485                 490

<210> SEQ ID NO 25
<211> LENGTH: 299
<212> TYPE: PRT
<213> ORGANISM: Segniliparus rugosus ATCC BAA-974

<400> SEQUENCE: 25

Met Lys Ser Tyr Ser Leu Gly Lys Phe Glu Asp Arg Ser Ile Asp Ser
1               5                   10                  15

Leu Ile Glu Glu Ala Ser Gly Leu Pro Asp Ser Ala Tyr Ser Ser Ala
            20                  25                  30

Tyr Gln Glu Tyr Ser Ile Gly Leu Trp Asp Thr Ala Thr Leu Trp Asn
        35                  40                  45

Glu Arg Gly Asn Glu Ser Gly Glu Val Ser His Ala Ala Ala Ala
50                  55                  60

Ala Pro Thr Ala Ile Gly Arg Ser Thr Pro Arg Leu Asn Glu Phe Val
65                  70                  75                  80

Arg Ala Lys Phe Asn Val Asp Val Leu Arg Ala Val Arg Leu Phe Arg
                85                  90                  95

Ala Arg Gln Gly Ala Ile Ile Pro His Arg Asp Tyr Leu Glu His
            100                 105                 110

Ser Asn Gly Phe Cys Arg Ile His Leu Pro Leu Val Thr Thr Pro Gly
        115                 120                 125

Ala Arg Asn Ser Glu Asn Asn Glu Val Tyr Arg Met Leu Pro Gly Glu
    130                 135                 140

Leu Trp Phe Leu Asp Ser Asn Glu Val His Ser Gly Gly Val Leu Asp
145                 150                 155                 160

Ser Gly Thr Arg Ile His Leu Val Leu Asp Phe Thr His Glu His Asn
                165                 170                 175

Glu Asn Pro Ala Ala Val Leu Lys Asn Ala Asp Arg Leu Arg Pro Ile
            180                 185                 190

Ala Arg Asp Pro Arg Ile Ser Arg Ser Lys Leu Asp His Glu Ala Leu
        195                 200                 205

Glu Ser Leu Ile Arg Gly Gly Arg Val Val Thr Leu Ala Met Trp Pro
    210                 215                 220

Ala Leu Val Gln Met Leu Ala Arg Ile His Leu Thr Ser Asp Ala His
225                 230                 235                 240

Pro Ala Glu Leu Tyr Asp Trp Leu Asp Asp Leu Ala Asp Arg Ser Gly
                245                 250                 255

Asn Asp Glu Leu Val Ala Glu Ala Arg Arg Met Arg Arg Tyr Phe Leu
            260                 265                 270

Thr Asp Gly Ile Ser Arg Thr Pro Ser Phe Glu Arg Phe Trp Arg Glu
        275                 280                 285

Leu Asp Ala Ala Arg Lys Gly Glu Leu Val Ser
    290                 295

<210> SEQ ID NO 26
<211> LENGTH: 299
```

<212> TYPE: PRT
<213> ORGANISM: Artificial Sequence
<220> FEATURE:
<223> OTHER INFORMATION: Mutant-type cis

<400> SEQUENCE: 26

Met Lys Ser Tyr Ser Leu Gly Lys Phe Glu Asp Arg Ser Ile Asp Ser
1               5                   10                  15

Leu Ile Glu Glu Ala Ser Gly Leu Pro Asp Ser Ala Tyr Ser Ser Ala
            20                  25                  30

Tyr Gln Glu Tyr Ser Ile Gly Leu Trp Asp Thr Ala Thr Leu Trp Asn
        35                  40                  45

Glu Arg Gly Asn Glu Ser Gly Glu Val Ser Glu His Ala Ala Ala Ala
    50                  55                  60

Ala Pro Thr Ala Ile Gly Arg Ser Thr Pro Arg Leu Asn Glu Phe Val
65                  70                  75                  80

Arg Ala Lys Phe Asn Val Asp Val Leu Arg Ala Val Arg Leu Phe Arg
                85                  90                  95

Ala Arg Gln Gly Ala Ile Ile Ile Pro His Arg Asp Tyr Leu Glu His
            100                 105                 110

Ser Asn Gly Phe Cys Arg Ile His Leu Pro Leu Val Thr Thr Pro Gly
        115                 120                 125

Ala Arg Asn Ser Glu Asn Asn Glu Val Tyr Arg Met Met Pro Gly Glu
    130                 135                 140

Leu Trp Phe Leu Asp Ser Asn Glu Val His Ser Gly Gly Val Leu Asp
145                 150                 155                 160

Ser Gly Thr Arg Ile His Leu Val Leu Asp Phe Thr His Glu His Asn
                165                 170                 175

Glu Asn Pro Ala Ala Val Leu Lys Asn Ala Asp Arg Leu Arg Pro Ile
            180                 185                 190

Ala Arg Asp Pro Arg Ile Ser Arg Ser Lys Leu Asp His Glu Ala Leu
        195                 200                 205

Glu Ser Leu Ile Arg Gly Gly Arg Val Val Thr Leu Ala Met Trp Pro
    210                 215                 220

Ala Leu Val Gln Met Leu Ala Arg Ile His Leu Thr Ser Asp Ala His
225                 230                 235                 240

Pro Ala Glu Leu Tyr Asp Trp Leu Asp Asp Leu Ala Asp Arg Ser Gly
                245                 250                 255

Asn Asp Glu Leu Val Ala Glu Ala Arg Arg Met Arg Arg Tyr Phe Leu
            260                 265                 270

Thr Asp Gly Ile Ser Arg Thr Pro Ser Phe Glu Arg Phe Trp Arg Glu
        275                 280                 285

Leu Asp Ala Ala Arg Lys Gly Glu Leu Val Ser
    290                 295

<210> SEQ ID NO 27
<211> LENGTH: 30
<212> TYPE: DNA
<213> ORGANISM: Artificial Sequence
<220> FEATURE:
<223> OTHER INFORMATION: Primer proCrocGX-SpeR

<400> SEQUENCE: 27
cttactagtt tatttcttat cgttctgcgg                                    30

<210> SEQ ID NO 28
<211> LENGTH: 30

```
<212> TYPE: DNA
<213> ORGANISM: Artificial Sequence
<220> FEATURE:
<223> OTHER INFORMATION: Primer proCX-SpeR

<400> SEQUENCE: 28
tctactagtt caggatttgc tgagttttc                                          30

<210> SEQ ID NO 29
<211> LENGTH: 30
<212> TYPE: DNA
<213> ORGANISM: Artificial Sequence
<220> FEATURE:
<223> OTHER INFORMATION: Primer rocGX-SpeF

<400> SEQUENCE: 29
atgactagtt cgaacagaaa gtaatcgtat                                         30

<210> SEQ ID NO 30
<211> LENGTH: 29
<212> TYPE: DNA
<213> ORGANISM: Artificial Sequence
<220> FEATURE:
<223> OTHER INFORMATION: Primer proCX-SpeF

<400> SEQUENCE: 30
tgaactagta gaaggagata tagatatgt                                          29
```

BIOLOGICAL METHOD FOR PRODUCING CIS-5-HYDROXY-L-PIPECOLIC ACID

CROSS-REFERENCE TO RELATED APPLICATION

This application is a Section 371 of International Application No. PCT/JP2013/066218, filed Jun. 12, 2013, which was published in the Japanese language on Dec. 19, 2013, under International Publication No. WO 2013/187438 A1, and the disclosure of which is incorporated herein by reference.

REFERENCE TO SEQUENCE LISTING SUBMITTED ELECTRONICALLY

This application contains a sequence listing, which is submitted electronically via EFS-Web As an ASCII formatted sequence listing with a file name "00714537.txt", creation date of Mar. 10, 2015, and having a size of 26 KB. The sequence listing submitted via EFs-Web is part of the specification and is herein incorporated by reference in its entirely.

TECHNICAL FIELD

The present invention relates to a gene recombinant microorganism having an ability to produce cis-5-hydroxy-L-pipecolic acid, and a method for producing cis-5-hydroxy-L-pipecolic acid using the microorganism.

BACKGROUND ART

Cis-5-hydroxy-L-pipecolic acid is a kind of modified amino acid, which has a structure consisting of L-pipecolic acid introduced with hydroxyl group, and it is a substance useful as a synthetic intermediate material of drugs.

Biological methods for producing L-pipecolic acid (or 2-piperidinecarboxylic acid or L-homoproline) have already been reported (Non-patent documents 1, 2, and Patent document 1). In these reports, L-pipecolic acid is produced from L-lysine by using *Escherichia coli* having the following polynucleotides (also referred to as DNAs).

a) A polynucleotide encoding a protein having the L-lysine 6-aminotransferase enzyme activity
b) A polynucleotide encoding a protein having the pyrroline-5-carboxylate reductase enzyme activity In these reports, the lat gene (SEQ ID NO: 1) derived from *Flavobacterium lutescens* IFO3084 strain is mentioned as an example of the polynucleotide of a) mentioned above, and the proC gene (SEQ ID NO: 3) derived from *Escherichia coli* is mentioned as an example of the polynucleotide of b) mentioned above. Since *Escherichia coli* originally has the proC gene, an *Escherichia coli* strain introduced with the lat gene and able to express it has an L-pipecolic acid-producing ability. Further, there have also been reported that the production rate of L-pipecolic acid was improved in *Escherichia coli* also having a DNA encoding a protein having the lysine-specific permease activity, for example, the lysP gene derived from *Escherichia coli* (SEQ ID NO: 4).

It has been reported that the CAC47686 protein derived from the alfalfa leguminous bacterium, *Sinorhizobium meliloti* 1021, has an ability to convert L-pipecolic acid into cis-5-hydroxy-L-pipecolic acid (Non-patent document 3). The amino acid sequence of this protein is registered at the database GenBank with an accession number of CAC47686. The nucleotide sequence encoding it is registered at the database GenBank with an accession number of AL591792 (SEQ ID NO: 6).

It has also been reported that the BAB52605 protein or CAC47686 protein derived from the *Lotus corniculatus* var. *japonicus* leguminous bacterium, *Mesorhizobium loti* MAFF303099, has an ability to convert L-proline into cis-4-hydroxyproline (Patent document 2). The amino acid sequence of the BAB52605 protein is registered at the database GenBank with an accession number of BAB52605. The nucleotide sequence encoding it is registered at the database GenBank with an accession number of BA000012 (SEQ ID NO: 7, loti gene).

PRIOR ART REFERENCES

Patent documents

Patent document 1: WO2001/048216 (Japanese Patent No. 4516712)
Patent document 2: WO2009/139365

Non-Patent Documents

Non-patent document 1: Biosci. Biotechnol. Biochem., 66 (3), 622-627, 2002
Non-patent document 2: Biosci. Biotechnol. Biochem., 66 (9), 1981-1984, 2002
Non-patent document 3: Adv. Synth. Catal., 353, 1375-1383, 2011

SUMMARY OF THE INVENTION

Object to be Achieved by the Invention

It is considered that the CAC47686 protein is a useful enzyme for synthesis of non-natural amino acids, but it suffers from the following problems.

Problem 1) When this protein is expressed in *Escherichia coli* by using a generally used method, it is insolubilized and inactivated.
Problem 2) When this protein is used for an in vitro reaction, it is promptly denatured.
Problem 3) When this protein is used for an in vitro reaction, in addition to cis-5-hydroxy-L-pipecolic acid, cis-3-hydroxypipecolic acid is also accumulated in an amount substantially equivalent to that of cis-5-hydroxy-L-pipecolic acid, from L-pipecolic acid.

According to Non-patent document 3, in order to express the CAC47686 protein in *Escherichia coli*, while avoiding the problem 1, for example, a cold shock promoter is used to induce expression of the protein at a low temperature, and GroEL/GroES of *Streptomyces coelicolor* is coexpressed. Further, it also mentions an idea that hydroxylation of L-pipecolic acid is attained by exposing L-pipecolic acid to live cells of the *Escherichia coli* expressing the foregoing protein as one of the methods for avoiding the problem 2. However, it does not describe whether this method was actually effective. Further, any method for avoiding the problem 3 has not been proposed. On the basis of the findings described above, it was considered that production of cis-5-hydroxy-L-pipecolic acid using *Escherichia coli* expressing the CAC47686 protein was difficult.

It was also considered that, like the CAC47686 protein, the BAB52605 protein also might have an ability to convert L-pipecolic acid into cis-5-hydroxy-L-pipecolic acid. However, as shown in the examples mentioned in this specification, it was found that the cis-5-hydroxy-L-pipecolic acid productivity of *Escherichia coli* expressing the BAB52605 protein encoded by the loti gene was comparatively low. The identity of the amino acid sequences of the BAB52605 protein and the CAC47686 protein is 66%.

Means for Achieving the Object

The amino acid sequence of the EFV12517 protein has been registered as a protein derived from *Segniliparus rugosus* ATCC BAA-974 at the database GenBank with an accession number of EFV12517. The nucleotide sequence encoding it is registered at the database GenBank with an accession number of ACZI01000186 (REGION: 1378 . . . 2229) (SEQ ID NO: 8, shortcis gene). The EFV12517 protein is annotated as aspartyl/asparaginyl beta-hydroxylase in the GenBank, and as shown in the examples mentioned in this specification, ability to convert L-pipecolic acid into cis-5-hydroxy-L-pipecolic acid could not be detected in *Escherichia coli* expressing the EFV12517 protein. However, it was found that *Escherichia coli* expressing the protein encoded by the polynucleotide (SEQ ID NO: 2, cis gene) expressed from a position upstream by 48 nucleotides (corresponding to 16 amino acids) from the annotation of the EFV12517 protein had the L-pipecolic acid cis-5-hydroxylase activity, and thus could convert L-pipecolic acid into cis-5-hydroxy-L-pipecolic acid, and the present invention was accomplished.

The present invention provides the followings.

[1] A method for producing cis-5-hydroxy-L-pipecolic acid or a pharmacologically acceptable salt thereof, or a solvate thereof, which comprises the step of producing cis-5-hydroxy-L-pipecolic acid by using L-pipecolic acid as a substrate with a microorganism containing any one of the polynucleotides of the following (A) to (F) in an expressible state:

(A) a polynucleotide having the nucleotide sequence of SEQ ID NO: 2, (B) a polynucleotide hybridizable with a polynucleotide comprising the nucleotide sequence complementary to the nucleotide sequence of SEQ ID NO: 2 under stringent conditions, and encoding a protein having an activity of catalyzing a reaction of generating cis-5-hydroxy-L-pipecolic acid by using L-pipecolic acid as a substrate;

(C) a polynucleotide showing an identity of 85% or higher to the nucleotide sequence of SEQ ID NO: 2, and encoding a protein having the activity of catalyzing the reaction of generating cis-5-hydroxy-L-pipecolic acid by using L-pipecolic acid as a substrate;

(D) a polynucleotide encoding a protein having the amino acid sequence of SEQ ID NO: 25;

(E) a polynucleotide encoding a protein having the amino acid sequence of SEQ ID NO: 25 including substitution, deletion, insertion, and/or addition of one or more amino acid residues, and having the activity of catalyzing the reaction of generating cis-5-hydroxy-L-pipecolic acid by using L-pipecolic acid as a substrate;

(F) a polynucleotide encoding a protein consisting of an amino acid sequence showing an identity of 85% or higher to the amino acid sequence of SEQ ID NO: 25, and having the activity of catalyzing the reaction of generating cis-5-hydroxy-L-pipecolic acid by using L-pipecolic acid as a substrate.

[2] The production method according to [1], wherein the microorganism further contains a polynucleotide encoding a protein having an activity of catalyzing a reaction of generating L-aminoadipate-delta-semialdehyde by using L-lysine as a substrate, and a polynucleotide encoding a protein having an activity of catalyzing a reaction of generating L-pipecolic acid by using delta-1-piperideine-6-carboxylic acid as a substrate, each in an expressible state; and which further comprises the step of generating L-aminoadipate-delta-semialdehyde by using L-lysine as a substrate, and then converting L-aminoadipate-delta-semialdehyde into delta-1-piperideine-6-carboxylic acid; and the step of generating L-pipecolic acid by using delta-1-piperideine-6-carboxylic acid as a substrate.

[3] The production method according to [2], wherein the polynucleotide encoding a protein having the activity of catalyzing the reaction of generating L-aminoadipate-delta-semialdehyde by using L-lysine as a substrate is derived from *Flavobacterium lutescens*.

[4] The production method according to [2] or [3], wherein the microorganism is *Escherichia coli*, and originally has a polynucleotide encoding a protein having the activity of catalyzing the reaction of generating L-pipecolic acid by using delta-1-piperideine-6-carboxylic acid as a substrate.

[5] A polynucleotide selected from the polynucleotides of the following (A) to (F):

(A) a polynucleotide having the nucleotide sequence of SEQ ID NO: 2, (B) a polynucleotide hybridizable with a polynucleotide comprising the nucleotide sequence complementary to the nucleotide sequence of SEQ ID NO: 2 under stringent conditions, and encoding a protein having an activity of catalyzing a reaction of generating cis-5-hydroxy-L-pipecolic acid by using L-pipecolic acid as a substrate;

(C) a polynucleotide showing an identity of 85% or higher to the nucleotide sequence of SEQ ID NO: 2, and encoding a protein having the activity of catalyzing the reaction of generating cis-5-hydroxy-L-pipecolic acid by using L-pipecolic acid as a substrate;

(D) a polynucleotide encoding a protein having the amino acid sequence of SEQ ID NO: 25;

(E) a polynucleotide encoding a protein having the amino acid sequence of SEQ ID NO: 25 including substitution, deletion, insertion, and/or addition of one or more amino acid residues, and having the activity of catalyzing the reaction of generating cis-5-hydroxy-L-pipecolic acid by using L-pipecolic acid as a substrate;

(F) a polynucleotide encoding a protein consisting of an amino acid sequence showing an identity of 85% or higher to the amino acid sequence of SEQ ID NO: 25, and having the activity of catalyzing the reaction of generating cis-5-hydroxy-L-pipecolic acid by using L-pipecolic acid as a substrate.

[6] A vector for transformation of a microorganism, which contains the polynucleotide according to [5].

[7] The vector for transformation of a microorganism according to [6], which further contains a polynucleotide encoding a protein having an activity of catalyzing a reaction of generating L-aminoadipate-delta-semialdehyde by using L-lysine as a substrate.

[8] The vector for transformation of a microorganism according to [6] or [7], which further contains a polynucleotide encoding a protein having an activity of catalyzing a reaction of generating α-ketoglutaric acid, and/or a protein having an activity of catalyzing a reaction of generating L-pipecolic acid by using delta-1-piperideine-6-carboxylic acid as a substrate.

[9] A gene recombinant microorganism transformed with the vector according to any one of [6] to [8].

[10] A gene recombinant *Escherichia coli*, which is transformed with the polynucleotide according to [5], and a polynucleotide encoding a protein having an activity of catalyzing a reaction of generating L-aminoadipate-delta-semialdehyde by using L-lysine as a substrate, and has an ability to generate cis-5-hydroxy-L-pipecolic acid by using L-lysine as a starting material.

[11] A protein selected from the proteins of the following (d) to (f):
(d) a protein having the amino acid sequence of SEQ ID NO: 25;
(e) a protein having the amino acid sequence of SEQ ID NO: 25 including substitution, deletion, insertion, and/or addition of one or more amino acid residues, and having an activity of catalyzing a reaction of generating cis-5-hydroxy-L-pipecolic acid by using L-pipecolic acid as a substrate;
(f) a protein consisting of an amino acid sequence showing an identity of 85% or higher to the amino acid sequence of SEQ ID NO: 25, and having the activity of catalyzing the reaction of generating cis-5-hydroxy-L-pipecolic acid by using L-pipecolic acid as a substrate.

[12] A method for producing cis-5-hydroxy-L-pipecolic acid or a pharmacologically acceptable salt thereof, or a solvate thereof, which comprises the step of allowing the protein according to [11] to act on L-pipecolic acid to generate cis-5-hydroxy-L-pipecolic acid.

[13] The production method according to [12], which further comprises:
the step of allowing a protein having an activity of catalyzing a reaction of generating L-aminoadipate-delta-semialdehyde by using L-lysine as a substrate to act on L-lysine to generate L-aminoadipate-delta-semialdehyde, and then converting L-aminoadipate-delta-semialdehyde into delta-1-piperideine-6-carboxylic acid; and
the step of allowing a protein having an activity of catalyzing a reaction of generating L-pipecolic acid by using delta-1-piperideine-6-carboxylic acid as a substrate to act on the obtained delta-1-piperideine-6-carboxylic acid to generate L-pipecolic acid.

[14] The gene recombinant microorganism or gene recombinant *Escherichia coli* according to [9] or [10], which has an ability to produce 50 mg or more of cis-5-hydroxy-L-pipecolic acid per 1 L of culture medium.

BRIEF DESCRIPTION OF THE DRAWINGS

FIGS. 3A-3E show the HPLC charts of authentic samples of cis-5-hydroxy-L-pipecolic acid and the products of the BL21(DE3)/pRSF-Cis strain (refer to Example 2); FIGS. 3A-3C show the HPLC charts for 200 μg/mL of authentic samples of cis-5-hydroxy-L-pipecolic acid; FIGS. 3D-3E show the HPLC charts for the products of the BL21(DE3)/pRSF-Cis strain;

FIG. 4A shows the LC/MS charts for a 200 μg/mL authentic sample of cis-5-hydroxy-L-pipecolic acid; and FIG. 4B shows the LC/MS charts for the products of the BL21(DE3)/pRSF-Cis strain; and FIGS. 5A-5C show the nucleotide sequences and amino acid sequences of the enzyme Lat, enzyme Cis, and mutant Cis, respectively.

MODES FOR CARRYING OUT THE INVENTION

Figure 1:
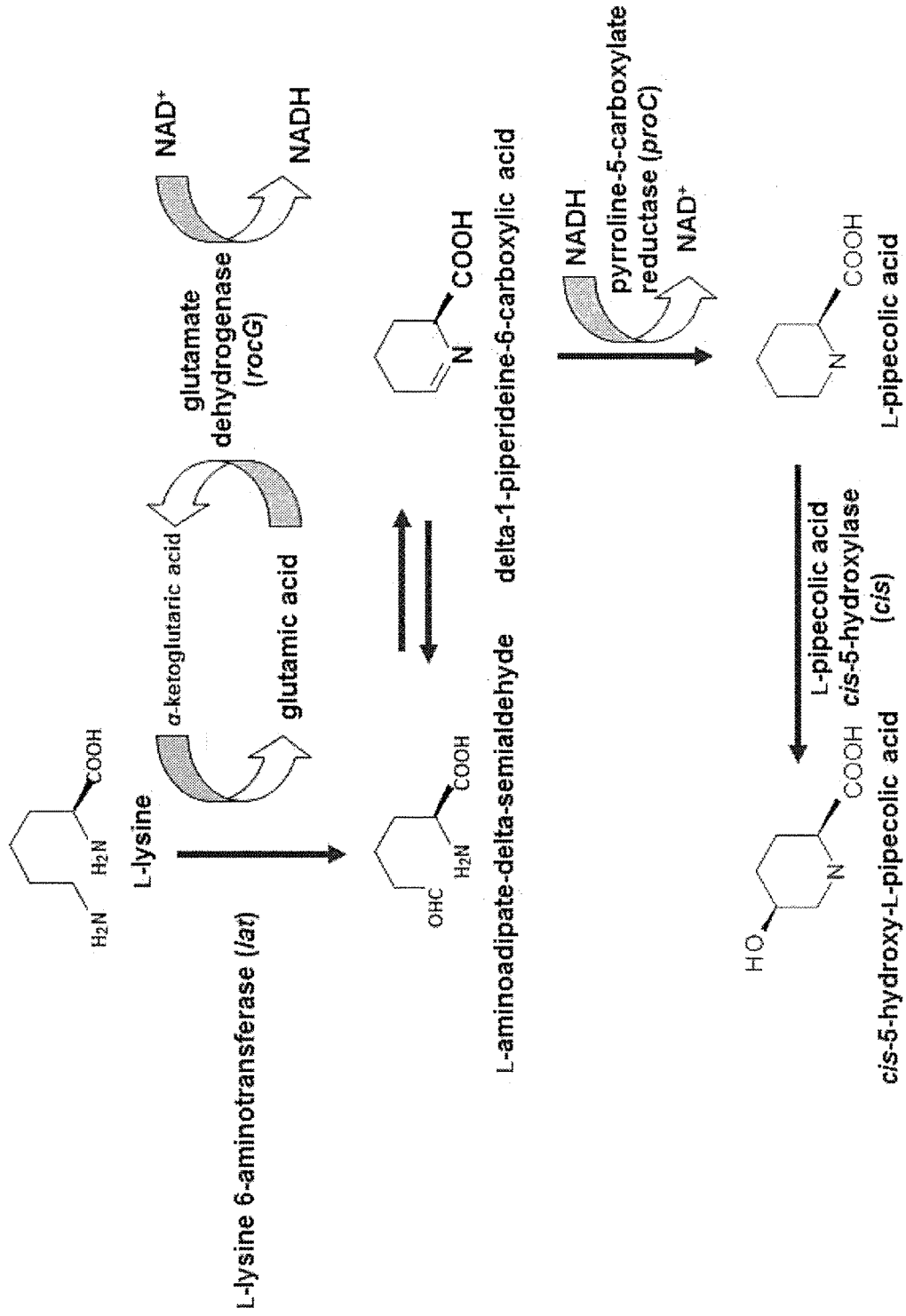
FIG. 1 shows an example of the production method of the present invention, indicating the conversion pathway from L-lysine to cis-5-hydroxy-L-pipecolic acid.

The present invention provides a method for producing cis-5-hydroxy-L-pipecolic acid represented by the following structural formula (I) or a pharmacologically acceptable salt thereof, or a solvate thereof.

Formula (I)

The method for producing cis-5-hydroxy-L-pipecolic acid of the present invention can comprise the following steps (1) to (3):
(1) the step of generating L-aminoadipate-delta-semialdehyde by using L-lysine as a substrate, and then converting L-aminoadipate-delta-semialdehyde into delta-1-piperideine-6-carboxylic acid;
(2) the step of generating L-pipecolic acid by using delta-1-piperideine-6-carboxylic acid as a substrate; and
(3) the step of generating cis-5-hydroxy-L-pipecolic acid by using L-pipecolic acid as a substrate.

The method for producing cis-5-hydroxy-L-pipecolic acid of the present invention comprises the step (3) mentioned above. The step (3) is a step of generating cis-5-hydroxy-L-pipecolic acid by using L-pipecolic acid as a substrate with a protein having the activity of catalyzing the reaction of generating cis-5-hydroxy-L-pipecolic acid by using L-pipecolic acid as a substrate, namely, the L-pipecolic acid cis-5-hydroxylase (Cis). This step can be biologically carried out by making an organism having the cis gene express Cis.

In the present invention, as the cis gene or the protein, any one of the polynucleotides of the following (A) to (F), or any one of the proteins of the following (d) to (f) can be used:
(A) a polynucleotide having the nucleotide sequence of SEQ ID NO: 2;
(B) a polynucleotide hybridizable with a polynucleotide comprising the nucleotide sequence complementary to the nucleotide sequence of SEQ ID NO: 2 under stringent conditions, and encoding a protein having the activity of catalyzing the reaction of generating cis-5-hydroxy-L-pipecolic acid by using L-pipecolic acid as a substrate;
(C) a polynucleotide showing an identity of 85% or higher to the nucleotide sequence of SEQ ID NO: 2, and encoding a protein having the activity of catalyzing the reaction of generating cis-5-hydroxy-L-pipecolic acid by using L-pipecolic acid as a substrate;
(D) a polynucleotide encoding a protein having the amino acid sequence of SEQ ID NO: 25;
(E) a polynucleotide encoding a protein having the amino acid sequence of SEQ ID NO: 25 including substitution, deletion, insertion, and/or addition of one or more amino acid residues, and having the activity of catalyzing the reaction of generating cis-5-hydroxy-L-pipecolic acid by using L-pipecolic acid as a substrate;

(F) a polynucleotide encoding a protein consisting of an amino acid sequence showing an identity of 85% or higher to the amino acid sequence of SEQ ID NO: 25, and having the activity of catalyzing the reaction of generating cis-5-hydroxy-L-pipecolic acid by using L-pipecolic acid as a substrate;

(d) a protein having the amino acid sequence of SEQ ID NO: 25;

(e) a protein having the amino acid sequence of SEQ ID NO: 25 including substitution, deletion, insertion, and/or addition of one or more amino acid residues, and having the activity of catalyzing the reaction of generating cis-5-hydroxy-L-pipecolic acid by using L-pipecolic acid as a substrate;

(f) a protein consisting of an amino acid sequence showing an identity of 85% or higher to the amino acid sequence of SEQ ID NO: 25, and having the activity of catalyzing the reaction of generating cis-5-hydroxy-L-pipecolic acid by using L-pipecolic acid as a substrate.

The nucleotide sequence of cis and the encoded amino acid sequence, which were identified by the inventors of the present invention and used in the examples mentioned in this specification, are shown as SEQ ID NOS: 2 and 25 in Sequence Listing.

Sequences showing high identity to the full length amino acid sequence of the Cis protein shown as SEQ ID NO: 25 were searched for, and it was found that the amino acid sequence shows an identity of 34% to the amino acid sequence of the CAC47686 protein encoded by the nucleotide sequence of SEQ ID NO: 6 (also referred to as "Meliloti protein" in the present invention), and an identity of 33% to the amino acid sequence of the BAB52605 protein encoded by the nucleotide sequence of SEQ ID NO: 7 (also referred to as "Loti protein" in the present invention). More precisely, the results of the identity analysis were Score=163 bits (413), Expect=6e-45, Method: Compositional matrix adjust, Identities=93/275 (34%), Positives=146/275 (53%), and Gaps=9/275 (3%) for the former, and Score=159 bits (402), Expect=3e-43, Method: Compositional matrix adjust, Identities=87/260 (33%), Positives=139/260 (53%), and Gaps=6/260 (2%) for the latter. Any other sequences showing identity higher than these were not retrieved. For the confirmation of the identity, blastp provided by NCBI was used.

The Cis protein used in the examples comprises an upstream region of the EFV12517 protein (also referred to as "Shortcis protein" in the present invention, which is encoded by the nucleotide sequence of SEQ ID NO: 8, and annotated as aspartyl/asparaginyl beta-hydroxylase at GenBank) encoded by 48 nucleotides, i.e., consisting of 16 amino acid residues. However, the ability to convert L-pipecolic acid into cis-5-hydroxy-L-pipecolic acid was not known for the Shortcis protein itself, and in fact, it could not be detected for it (refer to Example 2).

Further, the Meliloti protein, which shows an amino acid sequence identity of 34% to the Cis protein used in the examples, is known to have the ability to convert L-pipecolic acid into cis-5-hydroxy-L-pipecolic acid (Non-patent document 3 mentioned above), but it has been found that it has various problems as described above. On the other hand, according to the studies of the inventors of the present invention, it has been found that the Loti protein, which shows an amino acid sequence identity of 33% to the Cis protein used in the examples, shows comparatively low cis-5-hydroxy-L-pipecolic acid productivity, when it is expressed in *Escherichia coli* (refer to Example 3). In addition, the amino acid sequence identity between the Loti (BAB52605) protein and the Meliloti (CAC47686) protein is 66%, and thus the same difficulties as those found for the Meliloti protein are expected for the expression of the Loti protein in *Escherichia coli*, and the production of cis-5-hydroxy-L-pipecolic acid using the obtained protein.

According to one embodiment of the present invention, the cis gene and the encoded protein may be derived from a bacterium of the genus *Segniliparus*, more specifically, they may be derived from *Segniliparus rugosus*, and still more specifically, they may be derived from *Segniliparus rugosus* ATCC BAA-974.

The polynucleotides of (B) to (F) and proteins of (e) to (f) mentioned above should be called mutants of the cis gene and Cis protein used in the examples. Those skilled in the art can appropriately design such mutants in consideration of information on motif of the Cis protein used in the examples etc., and the fact that lack of the upstream sequence of 16 amino acid residues results in lack of the desired activity. According to the studies of the inventors of the present invention, it was found that the Cis protein used in the examples has the aspartyl/asparaginyl beta-hydroxylase region (positions 26 to 174), and L-proline 3-hydroxylase C-terminal region (positions 190 to 274). If a sequence is known, motif analysis thereof can be easily carried out by those skilled in the art by utilizing a website opened to public, for example, Pfam of GenomeNet (http://www.genome.jp/), or the like. Further, whether a certain protein has the activity of catalyzing the reaction of generating cis-5-hydroxy-L-pipecolic acid by using L-pipecolic acid as a substrate can be appropriately evaluated by those skilled in the art with referring to the descriptions of the present specification.

According to one embodiment of the present invention, a mutant Cis is used. An example of such a mutant Cis is the protein used in the examples of this specification, which consists of the amino acid sequence of SEQ ID NO: 26 encoded by the polynucleotide consisting of the nucleotide sequence of SEQ ID NO: 23. The nucleotide sequence of SEQ ID NO: 23 differs from the nucleotide sequence of cis (SEQ ID NO: 2) used in the examples in two nucleotides (among 897 nucleotides), and the amino acid sequence of SEQ ID NO: 26 differs from the amino acid sequence of Cis (SEQ ID NO: 25) used in the examples in one amino acid (among 299 amino acids). The identity between the amino acid sequences of SEQ ID NO: 26 and SEQ ID NO: 25 is 99.7%.

The amino acid sequence (SEQ ID NO: 26) of the mutant Cis used in the examples shows an identity of 34% to the amino acid sequence of the Meliloti protein encoded by the nucleotide sequence of SEQ ID NO: 6, and an identity of 29% to the amino acid sequence of the Loti protein encoded by the nucleotide sequence of SEQ ID NO: 7.

Concerning the expression "hybridizable under stringent conditions" used for a polynucleotide in the present invention, for any polynucleotide, the conditions of hybridization can be appropriately selected depending on the polynucleotide to be obtained, according to the descriptions of Molecular Cloning A Laboratory Manual 2nd ed. (Sambrook et al., Cold Spring Harbor Laboratory Press), and Hybridization of Nucleic Acid Immobilization on Solid Supports (ANALYTICAL BIOCHEMISTRY 138,267-284 (1984)), unless especially indicated. For example, when a DNA showing an identity of 85% or higher is to be obtained, hybridization can be performed at 45° C. in the presence of an SSC solution of 2-fold concentration and 50% formamide, and then the filter can be washed at 60° C. with an SSC solution of 0.1-fold concentration (SSC solution of 1-fold concentration has a composition of 150 mM sodium chloride and 15 mM sodium citrate). Further, when a DNA showing an identity of 90% or higher is to be obtained, hybridization can be performed at 50° C. in the presence of an SSC solution of 2-fold concentration and 50% formamide, and then the filter can be washed at 65° C. with an SSC solution of 0.1-fold concentration.

In the present invention, when the expression "amino acid sequence including substitution, deletion, insertion and/or addition of one or more amino acid residues" is used for a protein, for any proteins, the number of the amino acid residues to be substituted, or the like is not particularly limited so long as the protein consisting of the amino acid sequence has the desired function, unless especially indicated. However, the number may be about 1 to 9, or about 1 to 4, or in the case of substitution or the like of amino acid residues having similar properties, substitution or the like may occur for a further larger number of amino acid residues. Means for preparing a polynucleotide for a protein having such an amino acid sequence as mentioned above or the protein itself are well known to those skilled in the art.

When the term "identity" is used for nucleotide sequences or amino acid sequences in the present invention, for any nucleotide sequence or amino acid sequence, it means percentage of the number of the same nucleotide or amino acid residues commonly found at the corresponding positions in the two sequences optimally aligned, unless especially indicated. That is, the identity can be calculated in accordance with the following equation: Identity=(Number of positions at which the same residues locate in two sequences/Total number of positions)×100, and can be calculated by using a marketed algorithm. Such an algorithm is incorporated into the programs NBLAST and XBLAST described in Altschul et al., J. Mol. Biol., 215 (1990) 403-410. More precisely, search and analysis concerning identity of nucleotide sequence or amino acid sequence can be performed by using an algorithm or program well known to those skilled in the art (for example, BLASTN, BLASTP, BLASTX, ClustalW). The parameters used for executing each program can be appropriately chosen by those skilled in the art, or default parameters of each program may also be used. Specific procedures of these analysis methods are also well known to those skilled in the art.

In this specification, the term identity used for nucleotide sequences or amino acid sequences means, in any case, a sequence identity of at least 70%, preferably 80% or higher, more preferably 85% or higher, still more preferably 90% or higher, further preferably 95% or higher, still further preferably 97.5% or higher, particularly preferably 99% or higher.

The polynucleotides or genes, and proteins or enzymes used in the present invention can be prepared by those skilled in the art by using conventional techniques.

The method for producing cis-5-hydroxy-L-pipecolic acid of the present invention may comprise the step (1) mentioned above. The step (1) is a step of generating L-aminoadipate-delta-semialdehyde by using L-lysine as a substrate by using a protein having the activity of catalyzing the reaction of generating L-aminoadipate-delta-semialdehyde by using L-lysine as a substrate, namely, L-lysine 6-aminotransferase (Lat); and then converting L-aminoadipate-delta-semialdehyde into delta-1-piperideine-6-carboxylic acid. This step can be biologically performed by making an organism having the lat gene express Lat.

In the present invention, as the lat gene or the encoded protein, any one of the polynucleotides of the following (A') to (F'), or any one of the proteins of the following (d') to (f) can be used.

(A') a polynucleotide having the nucleotide sequence of SEQ ID NO: 1, (B') a polynucleotide hybridizable with a polynucleotide comprising the nucleotide sequence complementary to the nucleotide sequence of SEQ ID NO: 1 under stringent conditions, and encoding a protein having an activity of catalyzing the reaction of generating L-aminoadipate-delta-semialdehyde by using L-lysine as a substrate;

(C') a polynucleotide showing an identity of 85% or higher to the nucleotide sequence of SEQ ID NO: 1, and encoding a protein having the activity of catalyzing the reaction of generating L-aminoadipate-delta-semialdehyde by using L-lysine as a substrate;

(D') a polynucleotide encoding a protein having the amino acid sequence of SEQ ID NO: 24;

(E') a polynucleotide encoding a protein having the amino acid sequence of SEQ ID NO: 24 including substitution, deletion, insertion, and/or addition of one or more amino acid residues, and having the activity of catalyzing the reaction of generating L-aminoadipate-delta-semialdehyde by using L-lysine as a substrate;

(F') a polynucleotide encoding a protein comprising an amino acid sequence showing an identity of 85% or higher to the amino acid sequence of SEQ ID NO: 24, and having the activity of catalyzing the reaction of generating L-aminoadipate-delta-semialdehyde by using L-lysine as a substrate;

(d') a protein having the amino acid sequence of SEQ ID NO: 24;

(e') a protein having the amino acid sequence of SEQ ID NO: 24 including substitution, deletion, insertion, and/or addition of one or more amino acid residues, and having the activity of catalyzing the reaction of generating L-aminoadipate-delta-semialdehyde by using L-lysine as a substrate;

(f') a protein having an amino acid sequence showing an identity of 85% or higher to the amino acid sequence of SEQ ID NO: 24, and having the activity of catalyzing the reaction of generating L-aminoadipate-delta-semialdehyde by using L-lysine as a substrate.

The nucleotide sequence of lat and the encoded amino acid sequence derived from *Flavobacterium lutescens* IFO3084 are shown as SEQ ID NOS: 1 and 22 in Sequence Listing, respectively.

In the present invention, as the lat gene or the encoded protein, those derived from various organisms can be used. According to one embodiment of the present invention, the lat gene and the protein may be derived from a *Flavobacterium* bacterium, more specifically, *Flavobacterium lutescens*, further specifically, *Flavobacterium lutescens* IFO3084.

The method for producing cis-5-hydroxy-L-pipecolic acid of the present invention may comprise the step (2) mentioned above. The step (2) is a step of generating L-pipecolic acid by using delta-1-piperideine-6-carboxylic acid as a substrate using a protein having the activity of catalyzing the reaction of generating L-pipecolic acid by using delta-1-piperideine-6-carboxylic acid as a substrate, namely, pyrroline-5-carboxylate reductase (ProC). This step can be biologically carried out by using an organism having the proC gene.

The nucleotide sequence of proC and the encoded amino acid sequence derived from *Escherichia coli* are shown as SEQ ID NOS: 3 and 25 in Sequence Listing, respectively. As for proC, Patent document 1 mentioned above can be referred to.

ProC is an enzyme originally possessed by *Escherichia coli*. When the production method of the present invention is implemented by using *Escherichia coli*, as the enzyme used in the step (2), ProC originally possessed by *Escherichia coli* may be used, or for the purpose of enhancement of the enzyme or the like, a foreign ProC may be used. When the expression "contained in an expressible state" is used for a polynucleotide in the present invention, the polynucleotide is not limited to a foreign polynucleotide, but also may be a polynucleotide originally possessed by the host, unless especially indicated.

Any one or more or all of the aforementioned steps (1) to (3) of the method for producing cis-5-hydroxy-L-pipecolic acid of the present invention can be biologically performed. A typical example of the method biologically performed is the method performed in a microbial cell containing the required genes in expressible states. The microorganism used for the biological method for producing cis-5-hydroxy-L-pipecolic acid can be obtained by transforming a host microorganism with an appropriately constituted vector. The present invention also provides such gene recombinant microorganism and vector. The organism used for implementing the present invention is, for example, a microorganism, more specifically, for example, a procaryote, still more specifically, for example, *Escherichia coli*.

The term "gene recombinant microorganism" used in the present invention means a microorganism (bacterium, fungus, yeast, filamentous fungus, etc.) obtained by introducing, into a specific microorganism, a gene derived from another organism using a genetic recombination technique, unless especially indicated. The method for introducing a gene used therefor is not limited to a genetic recombination technique using a vector such as plasmid, but also may be such a method as homologous recombination.

According to the present invention, there can be obtained a gene recombinant microorganism having genes encoding a protein having the L-lysine 6-aminotransferase enzyme activity (Lat), a protein having the pyrroline-5-carboxylate reductase enzyme activity (ProC), and a protein having the L-pipecolic acid cis-5-hydroxylase activity (Cis), respectively, in expressible states, and able to directly produce cis-5-hydroxy-L-pipecolic acid from L-lysine. Further, by culturing such a gene recombinant microorganism and collecting cis-5-hydroxy-L-pipecolic acid from the culture medium, cis-5-hydroxy-L-pipecolic acid can be efficiently produced.

In any embodiment, the gene recombinant microorganism provided by the present invention may have a gene encoding a protein having lysine-specific permease protein activity (LysP) in an expressible state. It has been reported that use of LysP improved production rate of L-pipecolic acid in biological methods for producing L-pipecolic acid, and LysP may also be useful in a biological method for producing cis-5-hydroxy-L-pipecolic acid from the same point of view. The nucleotide sequence of the lysP gene derived from *Escherichia coli* is shown as SEQ ID NO: 4.

In any embodiment, the gene recombinant microorganism provided by the present invention may further contain a gene encoding a protein having an activity of catalyzing a reaction of generating α-ketoglutaric acid in an expressible state. Amino acid hydroxylases, of which typical example is L-pipecolic acid cis-5-hydroxylase, require α-ketoglutaric acid for the hydroxylation reaction catalyzed thereby (Non-patent document 3). Further, it is also known that L-lysine 6-aminotransferase also requires α-ketoglutaric acid for the transamination reaction catalyzed thereby, and converts it into glutamic acid (EC 2.6.1.36). Therefore, when L-pipecolic acid is produced from L-lysine using a microorganism that can express these proteins, it is expected to be important to regenerate α-ketoglutaric acid.

As enzyme that regenerates α-ketoglutaric acid from glutamic acid, glutamate dehydrogenase (EC 1.4.1.2) is known, and the reaction catalyzed by this enzyme can couple with the reaction catalyzed by L-lysine 6-aminotransferase. The nucleotide sequence of the rocG gene derived from *Bacillus subtilis* subsp. subtilis str. 168 is shown as SEQ ID NO: 5.

Hereafter, embodiments of the present invention will be explained more specifically.

The polynucleotide encoding a protein having the L-pipecolic acid cis-5-hydroxylase activity used for the biological method for producing cis-5-hydroxy-L-pipecolic acid of the present invention can be obtained from a cell of an appropriate microorganism by a method well known in this field (for example, the colony hybridization method described in Molecular Cloning A Laboratory Manual, 2nd ed.). Preferred examples of such a microorganism include a strain belonging to the genus *Segniliparus*, more specifically a strain belonging to *Segniliparus rugosus*, still more specifically *Segniliparus rugosus* ATCC BAA-974. Alternatively, as described in the examples of the present specification, a DNA encoding a protein having the L-pipecolic acid cis-5-hydroxylase activity may be artificially synthesized.

The polynucleotide encoding a protein having the L-pipecolic acid cis-5-hydroxylase activity, which was artificially synthesized in the examples, and expressed from the position upstream from the annotation of the EFV12517 protein by 48 nucleotides (corresponding to 16 amino acid residues) is as shown in SEQ ID NO: 2 mentioned in Sequence Listing. This DNA of SEQ ID NO: 2 contains the open reading frame (ORF) of cis (nucleotides 1 to 897).

The recombinant as one embodiment of the present invention is a gene recombinant microorganism containing polynucleotides encoding enzymes involved in the biosynthesis of L-pipecolic acid (for example, Lat, ProC, LysP, RocG), and a polynucleotide encoding L-pipecolic acid cis-5-hydroxylase (Cis), and it can be produced by incorporating both these DNAs into a host microorganism.

As the host, any microorganism into which the target DNAs can be incorporated, and which can produce the objective cis-5-hydroxy-L-pipecolic acid can be used without any particular restriction. Preferred examples of the microorganism include a strain belonging to *Escherichia coli*, for example, the *Escherichia coli* BL21(DE3) strain, and so forth.

The means for incorporating a foreign polynucleotide into a host, and expressing it is not particularly limited, and for example, methods described in Molecular Cloning A Laboratory Manual, 2nd ed., Current Protocols in Molecular Biology (edited by Frederick M. Ausubel et al., 1987), etc. can be used. The host-plasmid vector system is not particularly limited so long as a system that allows stable retention and expression of the objective polynucleotides in a host is chosen. Further, the plasmid may contain, in addition to the target polynucleotides, an autonomously replicable sequence, promoter sequence, terminator sequence, drug resistance gene, and so forth, and as for the type of the plasmid, the plasmid is not limited to autonomously replicable plasmid, but it may be an integration type plasmid having a sequence homologous to a certain region of the genome of the host planned to be used. The objective polynucleotide may be incorporated at any site on the plasmid or genome of the host microorganism.

When *Escherichia coli* is used as the host, examples of the autonomously replicable vector include pUC19, pRSFDuet-1, and so forth, examples of the promoter sequence include lac, T7, and so forth, examples of the terminator sequence include lacZ terminator, T7 terminator, and so forth, and examples of the drug resistance gene include ampicillin resistance gene, kanamycin resistance gene, and so forth.

When the present invention is implemented with a gene recombinant *Escherichia coli*, among the proteins involved in the biosynthesis of L-pipecolic acid, introduction of Lat and Cis is important, but whether ProC, LysP, and RocG are introduced or not can be appropriately determined in consideration of amount of the objective product, whether L-pipecolic acid is simultaneously produced or not, and degree thereof, if produced, utilization ratio of L-lysine as the starting material, and so forth.

By culturing gene recombinant microorganisms prepared as described above, evaluating productivities thereof for cis-5-hydroxy-L-pipecolic acid in a conventional manner, and selecting an appropriate recombinant, a useful strain that produces cis-5-hydroxy-L-pipecolic acid can be obtained. The product may be measured by the method described in the examples of the present specification.

The biological method for producing cis-5-hydroxy-L-pipecolic acid of the present invention is typically performed by culturing a gene recombinant microorganism. The culture conditions for the microorganism can be appropriately designed by those skilled in the art depending on the microorganism to be used. When *Escherichia coli* is used as the host, an appropriate amount of the microorganism can be inoculated into a commonly used medium containing antibiotics as a selection marker as required, and cultured at 20 to 40° C. for 6 to 72 hours, preferably 9 to 60 hours, more preferably 12 to 48 hours, with stirring or shaking at 100 to 400 rpm as required to allow proliferation of the cells. By supplying L-lysine or a salt thereof as the starting material, α-ketoglutaric acid or a salt thereof as required, and an appropriate inducer (for example, isopropylthio-β-galactoside (IPTG)) also as required, during or after the culture, and performing culture at 20 to 40° C. for 3 to 72 hours, preferably 4 to 60 hours, more preferably 6 to 48 hours, with stirring or shaking at 100 to 400 rpm as required, the objective substance is obtained in the culture medium. Timing of supply of L-lysine etc., and termination point of the culture can be appropriately determined by those skilled in the art in consideration of the production amount of the objective substance etc. For example, L-lysine etc. can be supplied, and culture can be terminated, after lapse of times determined beforehand on the basis of results of culture performed in a smaller scale in advance.

The initial concentration of L-lysine may be, for example, 2 to 32 g/L, more specifically 4 to 16 g/L, and the initial concentration of α-ketoglutaric acid may be, for example, 0 to 16 g/L, more specifically 0 to 8 g/L. Alternatively, the initial concentration of α-ketoglutaric acid may be, for example, 1 to 16 g/L, more specifically 2 to 8 g/L.

A preferred example of the gene recombinant *Escherichia coli* of the present invention is a gene recombinant *Escherichia coli* having an ability to produce 50 mg or more of cis-5-hydroxy-L-pipecolic acid per 1 L of culture medium.

Although the present invention may be explained for cis-5-hydroxy-L-pipecolic acid as an example of "cis-5-hydroxy-L-pipecolic acid or a pharmacologically acceptable salt thereof, or a solvate thereof", such explanation is also applied to the pharmacologically acceptable salt of cis-5-hydroxy-L-pipecolic acid and the solvate of them, unless especially indicated, and those skilled in the art can modify the method for producing cis-5-hydroxy-L-pipecolic acid into a method for producing a pharmacologically acceptable salt thereof or a solvate thereof by appropriately adding required steps. The "pharmacologically acceptable salt or a solvate thereof" referred to in the present invention include, as the salt, an alkali metal salt (for example, sodium salt, potassium salt), alkaline earth metal salt (for example, magnesium salt, calcium salt), ammonium salt, mono-, di-, or tri-(lower alkyl or hydroxyalkyl)ammonium salt (for example, ethanol ammonium salt, diethanol ammonium salt, triethanol ammonium salt, tromethamine salt), hydrochloride, hydrobromide, hydroiodide, nitrate, phosphate, sulfate, formate, acetate, citrate, oxalate, fumarate, maleate, succinate, malate, tartrate, trichloroacetate, trifluoroacetate, methanesulfonate, benzenesulfonate, p-toluenesulfonate, mesitylenesulfonate, and naphthalenesulfonate.

Further, the salt may be an anhydride or solvate, and examples of the solvate include hydrate, methanol solvate, ethanol solvate, propanol solvate, and 2-propanol solvate.

EXAMPLES

Hereafter, the present invention will be specifically explained with reference to examples. However, the present invention is not limited by these examples.

Example 1

Construction of pRSFduet-Cis

With reference to the nucleotide sequence of SEQ ID NO: 1, a primer lac-lat-NcoF2 (refer to SEQ ID NO: 9) having the NcoI site at the 5' end, and a primer lat-XhoR (refer to SEQ ID NO: 10) having the SpeI site at the 5' end were designed and prepared. Then, PCR was performed by using these two kinds of primers and the genomic DNA of the *Flavobacterium lutescens* IFO3084 strain as the template. PCR was performed by using KOD-Plus-Ver.2 (TOYOBO) with 30 cycles of three-step reaction comprising denaturation at 98° C. for 20 seconds, annealing at 60° C. for 20 seconds, and extension at 68° C. for 90 seconds. A DNA fragment having a size of about 1.5 kbp and containing lat was collected from the PCR amplification reaction mixture by using Wizard PCR Preps DNA Purification System (Promega). The obtained DNA fragment was digested with the restriction enzymes NcoI and XhoI to obtain a lat fragment.

With reference to the nucleotide sequence of SEQ ID NO: 4, a primer lysP-SD-XhoF (refer to SEQ ID NO: 11) having the XhoI site at the 5' end, and a primer lysP-KpnR (refer to SEQ ID NO: 12) having the KpnI site at the 5' end were designed and prepared (SIGMA GENOSYS). Then, PCR was performed in the same manner as mentioned above by using these two kinds of primers and the genomic DNA of the JM109 strain derived from the *Escherichia coli* K12 as the template. A DNA fragment having a size of about 1.5 kbp and containing lysP was collected from the PCR amplification reaction mixture. The obtained DNA fragment was digested with the restriction enzymes XhoI and KpnI to obtain a lysP fragment.

With reference to the nucleotide sequence of SEQ ID NO: 3, a primer proC-SD-KpnF (refer to SEQ ID NO: 13) having the KpnI site at the 5' end, and a primer proC-BamR (refer to SEQ ID NO: 14) having the BamHI site at the 5' end were designed and prepared. Then, PCR was performed in the same manner as mentioned above by using these two kinds of primers and the genomic DNA of the *Escherichia coli* K12 JM109 strain as the template. A DNA fragment having a size of about 1.0 kbp and containing proC was collected from the PCR amplification reaction mixture. The obtained DNA fragment was digested with the restriction enzymes KpnI and BamHI to obtain a proC fragment.

Four of components, a plasmid digestion product obtained by digesting pRSFDuet-1 (Novergen) with the restriction enzymes NcoI and BamHI, the lat fragment, the lysP fragment, and the proC fragment, were ligated by using DNA Ligation Kit ver.2 (Takara Bio) to construct a plasmid pRSF-LLP having the lat, lysP, and proC genes, and used to transform *E. coli* JM109 Competent Cells (Takara Bio).

Then, with reference to the nucleotide sequence of SEQ ID NO: 5, a primer rocG-SD-BamF (refer to SEQ ID NO: 15) having the BamHI site at the 5' end, and a primer rocG-XbaR (refer to SEQ ID NO: 16) having the XbaI site at the 5' end were designed and prepared. Then, PCR was performed in the same manner as mentioned above by using these two kinds of primers and the genomic DNA of the *Bacillus subtilis* subsp. *subtilis* str. 168 strain as the template. A DNA fragment having a size of about 1.3 kbp and containing rocG was collected from the PCR amplification reaction mixture. The obtained DNA fragment was digested with the restriction enzymes BamHI and XbaI to obtain a rocG fragment.

A plasmid digestion product obtained by digesting pRSF-LLP with the restriction enzymes BamHI and XbaI, and the rocG fragment were ligated to construct a plasmid pRSF-PA having the lat, lysP, proC, and rocG genes.

With reference to the nucleotide sequence of SEQ ID NO: 8, a primer segni-short-NdeF (refer to SEQ ID NO: 17) having the NdeI site at the 5' end, and a primer segni-cis-BglR (refer to SEQ ID NO: 18) having the BglII site at the 5' end were designed and prepared. Then, a gene was artificially synthesized as the nucleotide sequence of SEQ ID NO: 8 (GenScript), and by using this gene as the template, PCR was performed in the same manner as mentioned above. A DNA fragment having a size of about 0.9 kbp and containing cis was collected from the PCR amplification reaction mixture. The obtained DNA fragment was digested with the restriction enzymes NdeI and BglII to obtain a cisShort fragment.

A plasmid digestion product obtained by digesting pRSF-PA with the restriction enzymes NdeI and BglII was ligated with the cisShort fragment to construct a plasmid pRSF-CisShort having the lat, lysP, proC, and rocG genes as well as the gene (shortcis) encoding the EFV12517 protein.

With reference to the nucleotide sequence of SEQ ID NO: 2, a primer segni-cis-NdeF2 (refer to SEQ ID NO: 19) having the NdeI site at the 5' end, and a primer segni-cis-BglR (refer to SEQ ID NO: 18) having the BglII site at the 5' end were designed and prepared. Then, a gene was artificially synthesized as the nucleotide sequence of SEQ ID NO: 2 (GenScript), and by using this gene as the template, PCR was performed in the same manner as mentioned above. A DNA fragment having a size of about 0.9 kbp and containing cis was collected from the PCR amplification reaction mixture. The obtained DNA fragment was digested with the restriction enzymes NdeI and BglII to obtain a cis fragment.

Figure 2:
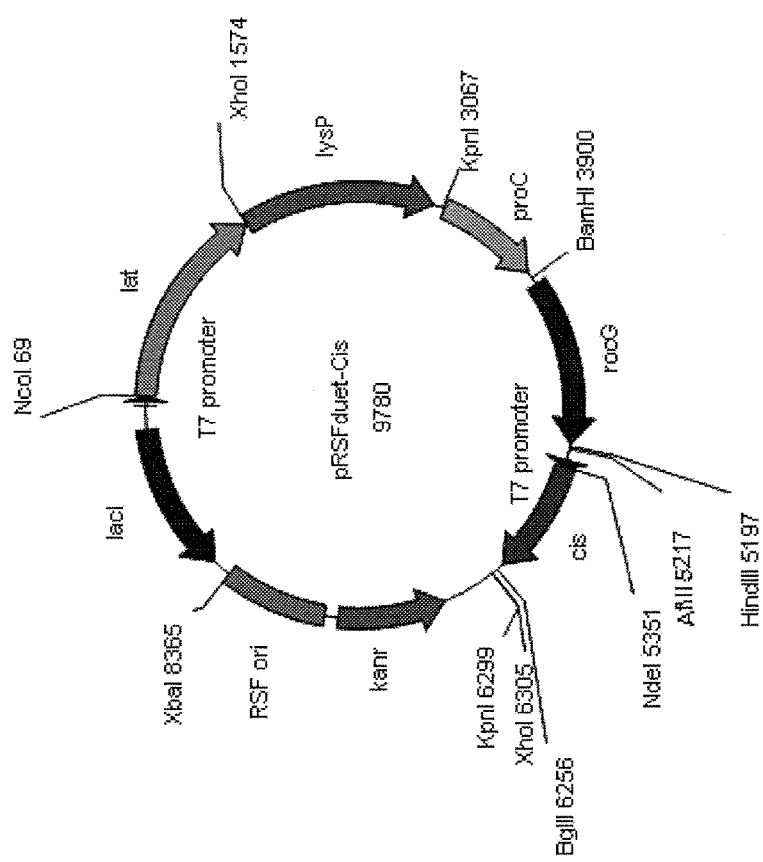
FIG. 2 shows the plasmid pRSF-Cis (refer to Example 1)
Figure 3A:
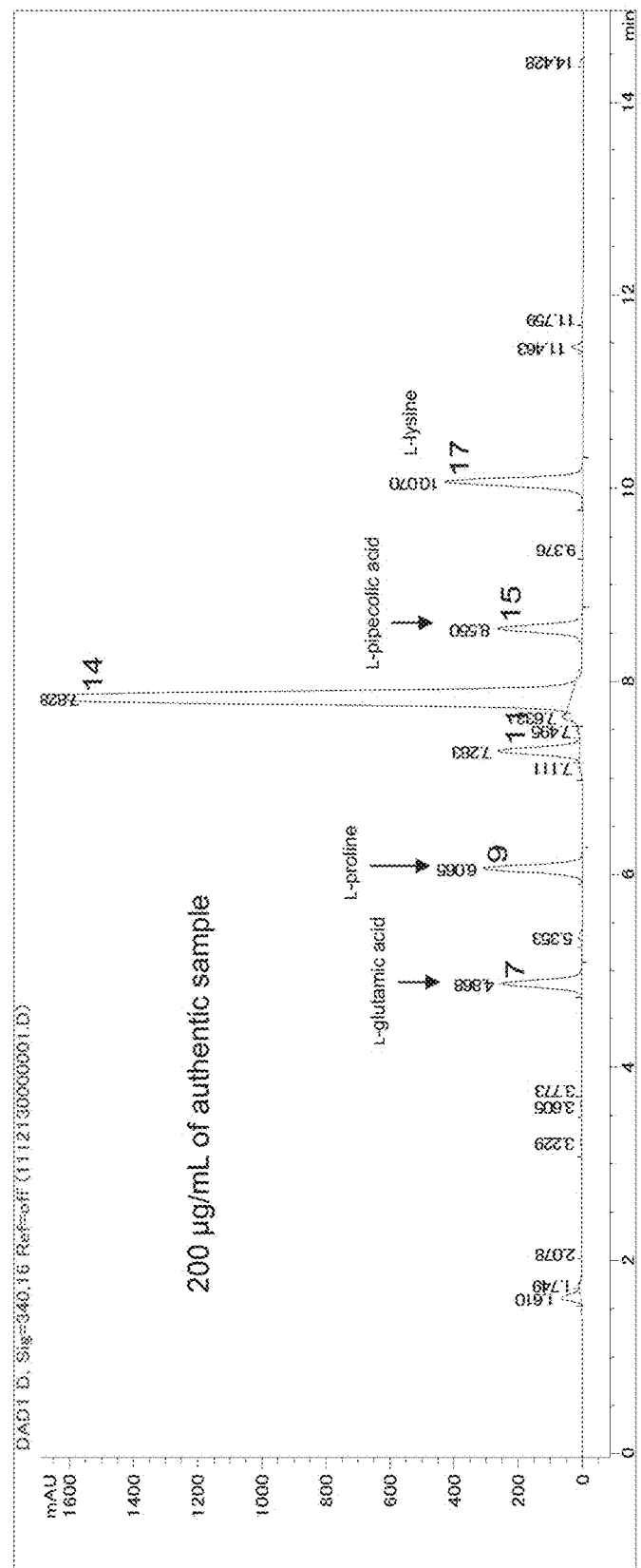
Figure 3C:
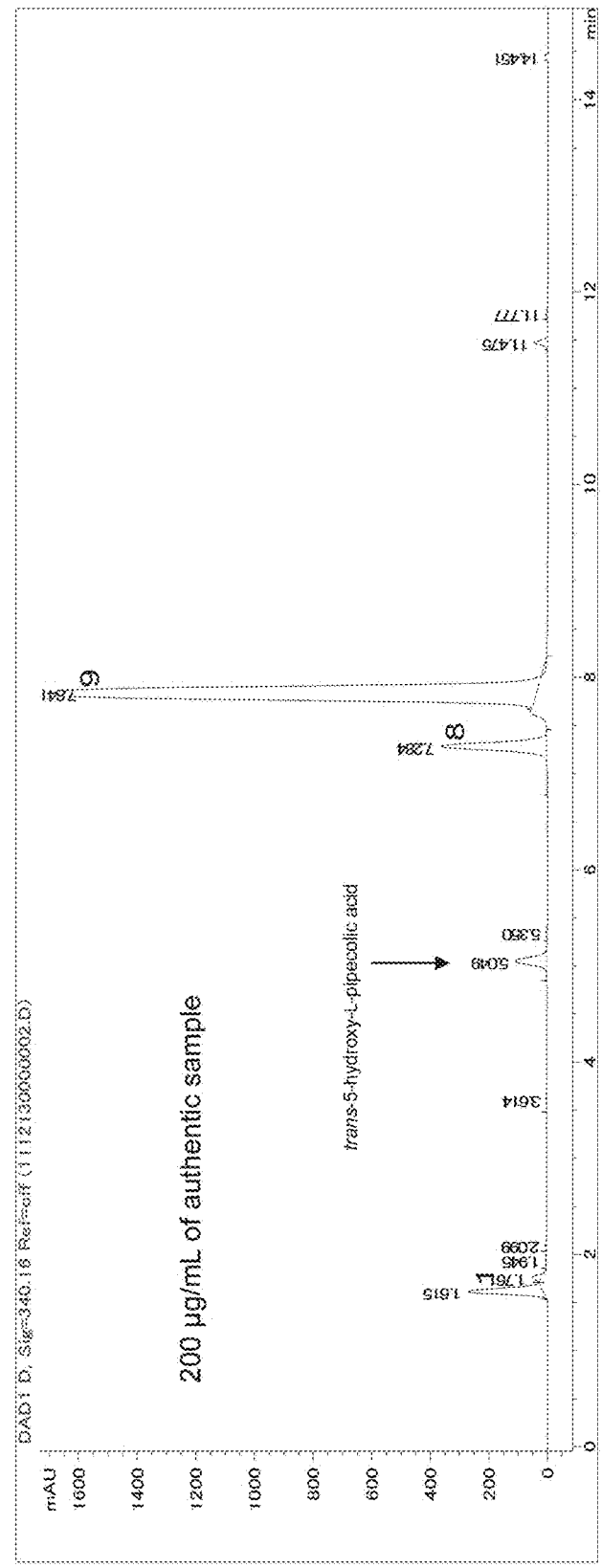
Figure 3D:
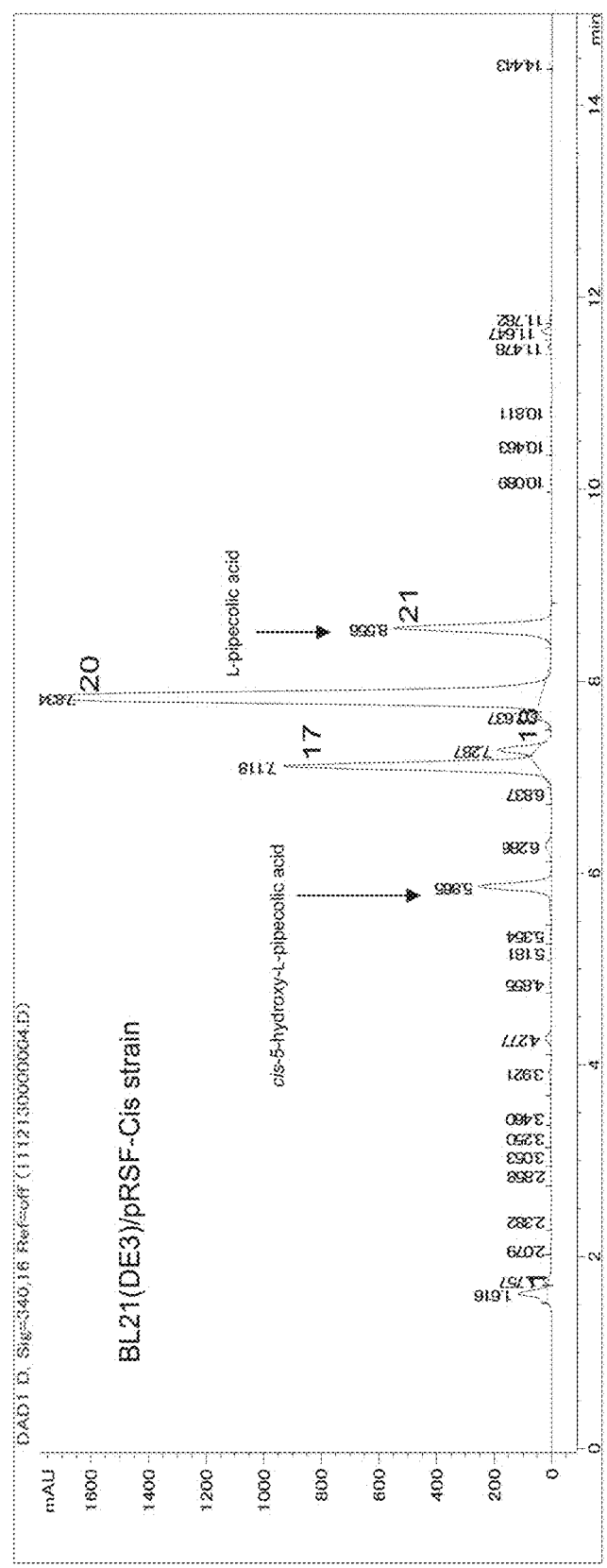
Figure 3E:
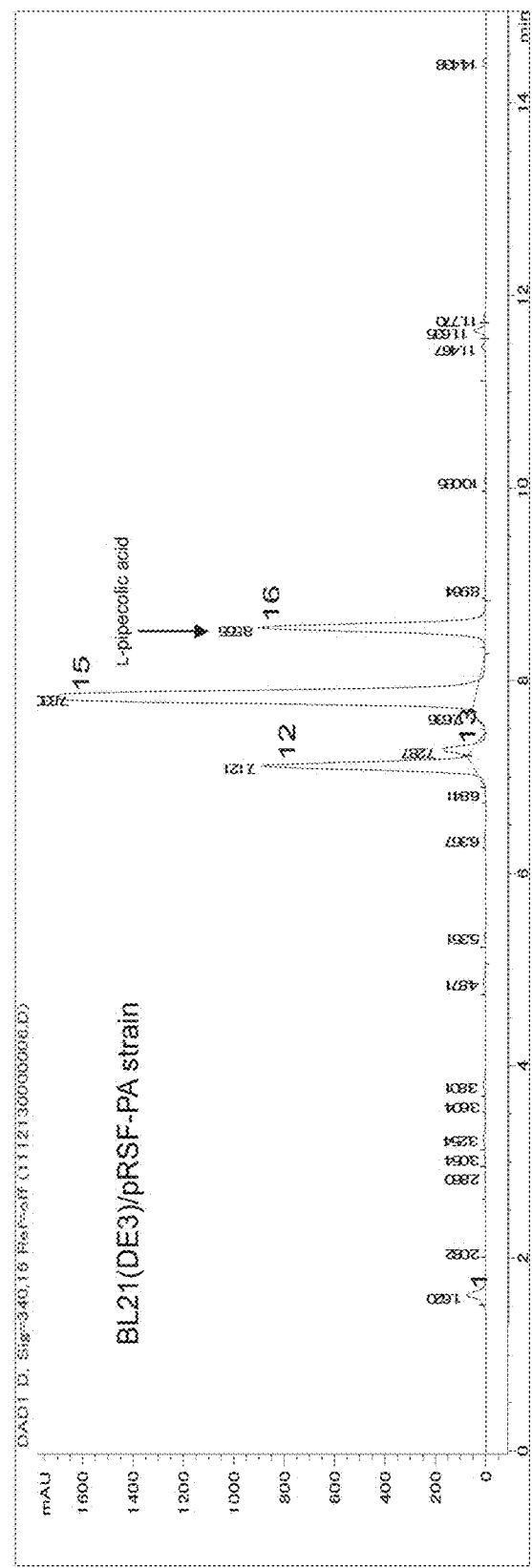
Figure 4A:
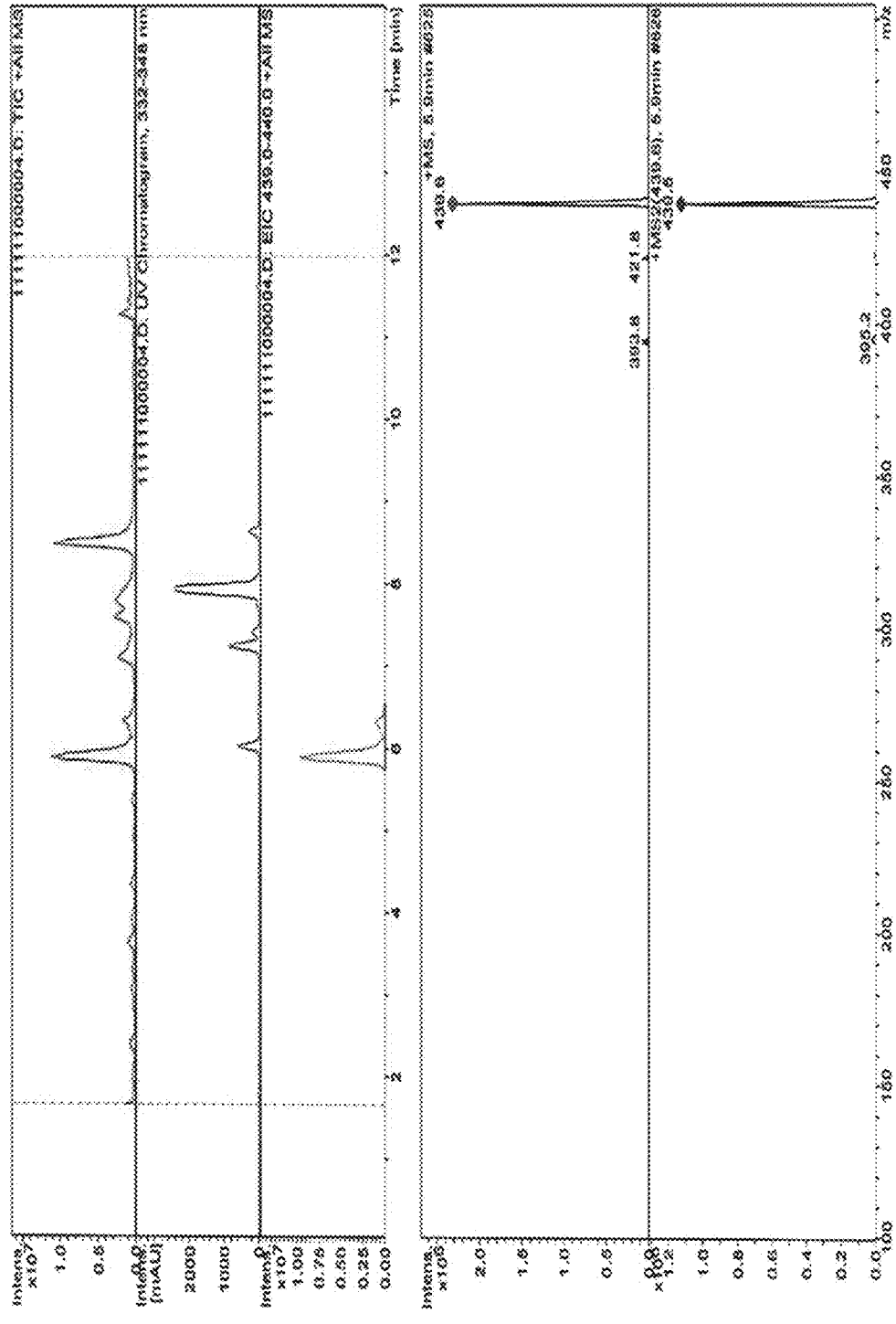
FIGS. 4A and 4B show the LC/MS charts of authentic samples of cis-5-hydroxy-L-pipecolic acid and the products of the BL21(DE3)/pRSF-Cis strain (refer to Example 2)
Figure 4B:
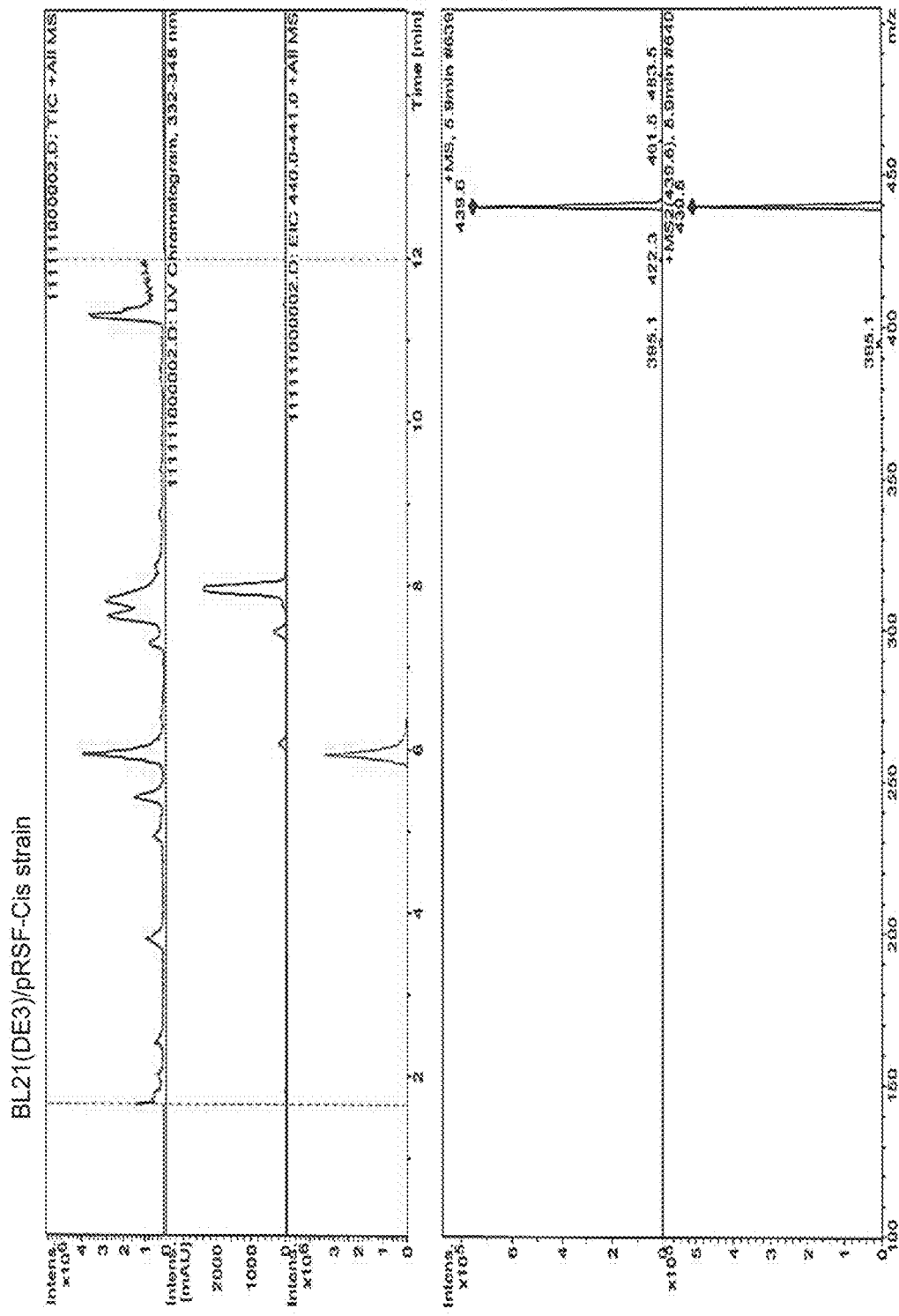

A plasmid digestion product obtained by digesting pRSF-PA with the restriction enzymes NdeI and BglII was ligated with the cis fragment to construct a plasmid pRSF-Cis having the lat, lysP, proC, rocG, and cis genes (FIG. 2).

With reference to the nucleotide sequence of SEQ ID NO: 1, a primer lac-lat-NcoF2 (refer to SEQ ID NO: 9) having the NcoI site at the 5' end, and a primer lat-(Spe)AflR2 (refer to SEQ ID NO: 20) having the AflII site at the 5' end were designed and prepared. Then, PCR was performed by using these two kinds of primers and the plasmid pRSF-Cis as the template. A DNA fragment having a size of about 1.5 kbp and containing lat was collected from the PCR amplification reaction mixture. The obtained DNA fragment was digested with the restriction enzymes NcoI and AflII to obtain a lat2 fragment.

A plasmid digestion product obtained by digesting pRSF-Cis with the restriction enzymes NcoI and AflII was ligated with the lat2 fragment to construct a plasmid pRSF-LatCis having the lat and cis genes.

With reference to the nucleotide sequence of SEQ ID NO: 7, a primer loti-SD-PacF (refer to SEQ ID NO: 21) having the NcoI site at the 5' end, and a primer loti -AvrR (refer to SEQ ID NO: 22) having the AvrII site at the 5' end were designed and prepared. Then, PCR was performed by using these two kinds of primers and the genomic DNA of the *Mesorhizobium loti* MAFF303099 strain as the template. A DNA fragment having a size of about 0.9 kbp and containing a gene encoding the BAB52605 protein was collected from the PCR amplification reaction mixture. The obtained DNA fragment was digested with the restriction enzymes PacI and AflII to obtain a loti fragment.

A plasmid digestion product obtained by digesting pRSF-Cis with the restriction enzymes PacI and AflII was ligated with the loti fragment to construct a plasmid pRSF-Loti having the lat, lysP, proC, rocG genes and a gene (loti) encoding the BAB52605 protein.

Finally, PCR was performed by using segni-cis-NdeF2 and segni-cis-BglR as the primers, as well as pRSF-Cis as the template with Diversify™ PCR Random Mutagenesis Kit (Clonteck) under Condition 5. A DNA fragment having a size of about 0.9 kbp was collected from the PCR amplification reaction mixture. The obtained DNA fragment was digested with the restriction enzymes NdeI and BglII to obtain a mutant cis fragment. A plasmid digestion product obtained by digesting pRSF-PA with the restriction enzymes NdeI and BglII was ligated with the mutant cis fragment to construct a plasmid pRSF-MutCisLibrary having the lat, lysP, proC, rocG, and mutant cis genes.

Example 2

Cis-5-hydroxy-L-pipecolic Acid Production Test 1

*Escherichia coli* One Shot BL21(DE3) Competent Cells (Life Technologies Japan) were transformed with each of the plasmids pRSF-Cis (FIG. 2), pRSF-CisShort, pRSF-PA, pRSF-LatCis, and pRSFDuet-1 to obtain BL21(DE3)/pRSF-Cis, BL21(DE3)/pRSF-CisShort, BL21(DE3)/pRSF-PA, BL21(DE3)/pRSF-LatCis, and BL21(DE3)/pRSFDuet-1 strains, respectively. These strains were each inoculated into the M9SEED liquid medium (3.39% $Na_2HPO_4$, 1.5% $KH_2PO_4$, 0.25% calcium chloride, 0.5% ammonium chloride, 1% casamino acid, 0.002% thymine, 0.1 mM calcium chloride, 0.1 mM iron sulfate, 0.4% glucose, and 0.001 mM magnesium chloride) containing kanamycin sulfate (25 µg/ml), and cultured at 30° C. for 22 hours with shaking at 220 rpm. This culture medium (10 µL) was added to the M9Cis medium (3.39% $Na_2HPO_4$, 1.5% $KH_2PO_4$, 0.25% calcium chloride, 0.5% ammonium chloride, 1% casamino acid, 0.002% thymine, 0.1 mM calcium chloride, 0.1 mM iron sulfate, 0.01% 80 µg/ml 5-aminolevulinic acid) containing kanamycin sulfate (30 μg/mL) and Overnight Express Autoinduction Systems (Merck), and culture was performed at 30° C. for 9 hours with shaking at 220 rpm. Then, 40% L-lysine hydrochloride (10 μL; final concentration, 8 g/L), 20% α-ketoglutaric acid (10 μL; final concentration, 4 g/L), 100 mM IPTG (0.5 μL; final concentration, 0.1 mM), and 50% glycerol (5 μL; final concentration, 0.5%) were added, and culture was further performed at 30° C. with shaking at 220 rpm. Twenty-four hours after the start of the culture, centrifugation supernatant of the culture medium was collected, and used for the preparation of LC/MS analysis samples.

Each sampled solution was FDLA-ized by the following method using Nα-(5-fluoro-2,4-dinitrophenyl)-L-leucinamide (L-FDLA, Tokyo Chemical Industry).

To 20 μL of the centrifugation supernatant of the sampled solution diluted 10 time, 1 M NaHCO$_3$ (6.25 μL) and 1% L-FDLA solution in acetone (30 μL) were added, and the mixture was kept warm at 37° C. for 1 hour. The reaction was terminated by adding 1 N HCl (6.25 μL), and acetonitrile (60 μL) was added to the mixture for dilution to obtain an FDLA-ized solution.

Amounts of L-lysine, L-pipecolic acid, and cis-5-hydroxy-L-pipecolic acid contained in the obtained FDLA-ized solution were measured by HPLC and LC/MS. The HPLC and LC/MS analysis charts are shown in FIGS. 3A-3E and 4A-4B. The quantification results are shown in Table 1. The HPLC and LC/MS measurement conditions are shown below.

Analysis Conditions
Column: CAPCELLPAK C18 SG120, 4.6×150 mm, 5 μm
Flow rate: 1.0 mL/minute
Mobile phase: A=0.1% acetic acid, B=acetonitrile Gradient: 0 to 9 minutes (B=30 to 65%), 9.01 to 12 minutes (B=90%), 12.01 to 15 minutes (B=30%)
Detection: 340 nm
Injection volume: 5 μL
Column temperature: 40° C.
MS: Agilent 6320 (Ion trap)
Mode: ESI/APCI positive
Scan Range: m/z 100 to 900
Analytical time: 15 minutes
Retention time:
L-Lysine, 10.0 minutes
L-Pipecolic acid, 8.5 minutes
Cis-5-hydroxy-L-pipecolic acid, 5.8 minutes

TABLE 1

| Strain | Accumulated amount (g/L) | | |
|---|---|---|---|
| | Cis-5-hydroxy-L-pipecolic acid | L-Pipecolic acid | L-Lysine |
| BL21(DE3)/pRSF-Cis | 3.4 | 4.2 | 0.2 |
| BL21(DE3)/pRSF-CisShort | N.D. | 6.2 | 0.3 |
| BL21(DE3)/pRSF-LatCis | 2.3 | 0.8 | 5.6 |
| BL21(DE3)/pRSF-PA | N.D. | 6.9 | 0.2 |
| BL21(DE3)/pRSFDuet-1 | N.D. | N.D. | 8.9 |

N.D. means "not detected".

As a result, whereas production of L-pipecolic acid and cis-5-hydroxy-L-pipecolic acid could not be confirmed for the BL21(DE3)/pRSFDuet-1 strain, the BL21(DE3)/pRSF-CisShort strain (containing the lat, lysP, proC, rocG, and shortcis genes on the plasmid) and the BL21(DE3)/pRSF-PA strain (containing the lat, lysP, proC, and rocG genes on the plasmid) produced L-pipecolic acid. Further, the BL21 (DE3)/pRSF-Cis strain (containing the lat, lysP, proC, rocG, and cis genes on the plasmid), and the BL21(DE3)/pRSF-LatCis strain (containing the kit and cis genes on the plasmid) produced cis-5-hydroxy-L-pipecolic acid and L-pipecolic acid.

These results demonstrated that introduction of the cis gene into a strain having an L-pipecolic acid-producing ability (coexpression of the lat gene and the cis gene in this case) enables direct production of cis-5-hydroxy-L-pipecolic acid, and further coexpression of the lysP, proC, and rocG genes can improve the productivity. As the standard sample of L-pipecolic acid, L-Pipecolic Acid (Tokyo Chemical Industry) was used, and as the standard sample of cis-5-hydroxy-L-pipecolic acid, (2S,5S)-5-Hydroxypipecolic Acid (SV ChemBIOTECH. INC) was used.

As described above, whereas the ability to convert L-pipecolic acid into cis-5-hydroxy-L-pipecolic acid could not be detected for the *Escherichia coli* expressing the EFV12517 protein encoded by the shortcis gene, the *Escherichia coli* expressing the protein encoded by the polynucleotide (cis gene) expressed from the position upstream from the annotation of the EFV12517 protein by 48 nucleotides (corresponding to 16 amino acid residues) had the L-pipecolic acid cis-5-hydroxylase activity for converting L-pipecolic acid into cis-5-hydroxy-L-pipecolic acid. Homologies of the amino acid sequence of the protein encoded by this cis gene to the amino acid sequences of the CAC47686 protein and BAB52605 protein were 34% and 33%, respectively.

On the basis of the aforementioned results, it was considered that it was difficult to expect from known information that *Escherichia coli* expressing the protein encoded by the cis gene has the L-pipecolic acid cis-5-hydroxylase activity for converting L-pipecolic acid into cis-5-hydroxy-L-pipecolic acid.

Example 3

Cis-5-hydroxy-L-pipecolic Acid Production Test 2

*Escherichia coli* One Shot BL21(DE3) Competent Cells were transformed with each of the plasmids pRSF-Cis, and pRSF-Loti to obtain strains BL21(DE3)/pRSF-Cis, and BL21(DE3)/pRSF-*Loti*, respectively. Further, one of the strains obtained by transforming *Escherichia coli* One Shot BL21(DE3) Competent Cells with the plasmid pRSF-MutCisLibrary was used as BL21(DE3)/pRSF-MutCis1. Culture of these strains and analysis were performed in the same manners as those of Example 2 to measure the amounts of L-pipecolic acid and cis-5-hydroxy-L-pipecolic acid. The measurement results are shown in Table 2.

TABLE 2

| Strain | Accumulated amount (g/L) | | |
|---|---|---|---|
| | Cis-5-hydroxy-L-pipecolic acid | L-Pipecolic acid | L-Lysine |
| BL21(DE3)/pRSF-Cis | 2.9 | 3.8 | N.D. |
| BL21(DE3)/pRSF-Loti | 0.1 | 6.5 | N.D. |
| BL21(DE3)/pRSF-MutCis1 | 3.0 | 3.6 | N.D. |

N.D. means "not detected".

As a result, the cis-5-hydroxy-L-pipecolic acid production amount of the BL21(DE3)/pRSF-Loti strain (containing the lat, lysP, proC, rocG, and loti genes on the plasmid) was about 1/30 of that of the BL21(DE3)/pRSF-Cis strain (containing the lat, lysP, proC, rocG, and cis genes on the plasmid). This result demonstrated that, when *Escherichia coli* expressing the BAB52605 protein encoded by the loti gene is used, the amount of cis-5-hydroxy-L-pipecolic acid to be obtained is comparatively small.

On the other hand, even the BL21(DE3)/pRSF-MutCis1 strain (containing the lat, lysP, proC, rocG, and mutant cis genes on the plasmid) showed a cis-5-hydroxy-L-pipecolic acid production amount equivalent to or higher than that obtained with the BL21(DE3)/pRSF-Cis strain. The result of the nucleotide sequence analysis of this mutant cis gene performed by using BigDye Terminator v3.1 Cycle Sequencing Kit (Applied Biosystems) is shown as SEQ ID NO: 23. As a result, the homology between the cis gene nucleotide sequence and the mutant cis gene nucleotide sequence was 99.7%, since they were different in 2 nucleotides among the 897 nucleotides in total. This result demonstrated that it is possible to produce cis-5-hydroxy-L-pipecolic acid by using *Escherichia coli* expressing a protein encoded by a gene showing a homology of 99.7% or higher to the cis gene nucleotide sequence.

Example 4

Cis-5-hydroxy-L-pipecolic Acid Production Test 3

*Escherichia coli* One Shot BL21(DE3) Competent Cells were transformed with each of the plasmids pRSF-Cis, and pRSF-CisΔproCΔrocG to obtain strains BL21(DE3)/pRSF-Cis, and BL21(DE3)/pRSF-CisΔproCΔrocG, respectively. Culture of these strains and analysis were performed in the same manners as those of Example 2 to measure the amounts of L-pipecolic acid and cis-5-hydroxy-L-pipecolic acid. The measurement results are shown in Table 3.

TABLE 3

| Strain | Accumulated amount (g/L) | | |
| --- | --- | --- | --- |
|  | Cis-5-hydroxy-L-pipecolic acid | L-Pipecolic acid | L-Lysine |
| BL21(DE3)/pRSF-Cis | 3.8 | 4.6 | 0 |
| BL21(DE3)/pRSF-CisΔproCΔrocG | 2.6 | 0 | 7.6 |

As a result, the cis-5-hydroxy-L-pipecolic acid production amount of the BL21(DE3)/pRSF-CisΔproCΔrocG strain (containing the lat, lysP, and cis genes on the plasmid) was about ⅔ of that of the BL21(DE3)/pRSF-Cis strain (containing the lat, lysP, proC, rocG, and cis genes on the plasmid). This result demonstrated that presence of the proC and rocG genes on the plasmid in addition to the lat and lysP genes provides a larger amount of the obtained cis-5-hydroxy-L-pipecolic acid.

Example 5

Cis-5-hydroxy-L-pipecolic Acid Production Test 4

In order to delete the proC gene, rocG gene, or both of these genes of the plasmid pRSF-Cis, the following primers were produced.

```
Primer proCrocGX-SpeR (refer to SEQ ID NO: 27)

Primer proCX-SpeR (refer to SEQ ID NO: 28)

Primer rocGX-SpeF (refer to SEQ ID NO: 29)

Primer proCX-SpeF (refer to SEQ ID NO: 30)
```

The plasmid pRSF-CisΔproC corresponding to the plasmid pRSF-Cis of which proC gene is deleted was produced as follows. By using the primer proCX-SpeF and the primer proCrocGX-SpeR, as well as pRSF-Cis as the template, PCR was performed. A DNA fragment corresponding to the plasmid pRSF-Cis of which proC gene is deleted was collected from the PCR amplification reaction mixture. The obtained DNA fragment was digested with the restriction enzyme SpeI, and the product was self-ligated to construct pRSF-CisΔproC, which was used to transform *E. coli* JM109 Competent Cells (Takara Bio). Similarly, the plasmid pRSF-CisΔrocG corresponding to the plasmid pRSF-Cis of which rocG gene is deleted was prepared by using the primer rocGX-SpeF and the primer proCX-SpeR, and the plasmid pRSF-CisΔproCΔrocG corresponding to the plasmid pRSF-Cis of which proC gene and rocG gene are deleted was produced by using the primer rocGX-SpeF and the primer proCrocGX-SpeR.

*Escherichia coli* One Shot BL21(DE3) Competent Cells (Life Technologies Japan) were transformed with each of the plasmids pRSF-Cis, pRSF-CisΔproC, pRSF-CisΔrocG, and pRSF-CisΔproCΔrocG to obtain BL21(DE3)/pRSF-Cis, BL21(DE3)/pRSF-CisΔproC, BL21(DE3)/pRSF-CisΔrocG, and BL21(DE3)/pRSF-CisΔproCΔrocG, respectively. These strains were each inoculated into the M9SEED liquid medium (3.39% $Na_2HPO_4$, 1.5% $KH_2PO_4$, 0.25% calcium chloride, 0.5% ammonium chloride, 1% casamino acid, 0.002% thymine, 0.1 mM calcium chloride, 0.1 mM iron sulfate, 0.4% glucose, and 0.001 mM magnesium chloride) containing kanamycin sulfate (25 μg/ml), and cultured at 30° C. for 9 hours with shaking at 220 rpm. This culture medium (10 μL) was added to the M9Cis medium (3.39% $Na_2HPO_4$, 1.5% $KH_2PO_4$, 0.25% calcium chloride, 0.5% ammonium chloride, 1% casamino acid, 0.002% thymine, 0.1 mM calcium chloride, 0.1 mM iron sulfate, 0.01% 80 μg/ml 5-aminolevulinic acid) containing kanamycin sulfate (30 μg/mL), L-lysine hydrochloride (final concentration, 8 g/L), α-ketoglutaric acid (final concentration, 2 g/L) and Overnight Express Autoinduction Systems (Merck), and culture was performed at 30° C. for 15 hours with shaking at 220 rpm. Then, 40% L-lysine hydrochloride (5 μL; final concentration, 4 g/L), 20% α-ketoglutaric acid (5 μL; final concentration, 2 g/L), 100 mM IPTG (0.5 μL; final concentration, 0.1 mM), and 50% glycerol (5 μL; final concentration, 0.5%) were added, and culture was further performed at 30° C. with shaking at 220 rpm. Thirty-nine hours after the start of the culture, centrifugation supernatant of the culture medium was collected, and used for the preparation of LC/MS analysis samples. The measurement results are shown in Table 4.

TABLE 4

| Strain | Accumulated amount (g/L) | | |
| --- | --- | --- | --- |
|  | Cis-5-hydroxy-L-pipecolic acid | L-Pipecolic acid | L-Lysine |
| BL21(DE3)/pRSF-Cis | 1.3 | 1.0 | 4.2 |
| BL21(DE3)/pRSF-CisΔproC | 1.0 | 1.0 | 4.4 |
| BL21(DE3)/pRSF-CisΔrocG | 1.5 | 1.2 | 4.0 |

TABLE 4-continued

|  | Accumulated amount (g/L) | | |
| --- | --- | --- | --- |
| Strain | Cis-5-hydroxy-L-pipecolic acid | L-Pipecolic acid | L-Lysine |
| BL21(DE3)/pRSF-CisΔproCΔrocG | 1.5 | 1.2 | 2.7 |

As a result, under these culture conditions, the cis-5-hydroxy-L-pipecolic acid production amounts obtained with BL21(DE3)/pRSF-CisΔrocG and BL21(DE3)/pRSF-CisΔproCΔrocG were larger than that obtained with BL21(DE3)/pRSF-Cis.

Sequence Listing Free Text

SEQ ID NO: 1, Nucleotide sequence of lat
SEQ ID NO: 2, Nucleotide sequence of cis
SEQ ID NO: 3, Nucleotide sequence of proC
SEQ ID NO: 4, Nucleotide sequence of lysP
SEQ ID NO: 5, Nucleotide sequence of rocG
SEQ ID NO: 6, Nucleotide sequence of meliloti
SEQ ID NO: 7, Nucleotide sequence of loti
SEQ ID NO: 8, Nucleotide sequence of shortcis
SEQ ID NO: 9, Primer lac-lat-NcoF2
SEQ ID NO: 10, Primer lat-XhoR
SEQ ID NO: 11, Primer lysP-SD-XhoF
SEQ ID NO: 12, Primer lysP-KpnR
SEQ ID NO: 13, Primer proC-SD-KpnF
SEQ ID NO: 14, Primer proC-BamR
SEQ ID NO: 15, Primer rocG-SD-BamF
SEQ ID NO: 16, Primer rocG-XbaR
SEQ ID NO: 17, Primer segni-short-NdeF
SEQ ID NO: 18, Primer segni-cis-BglR
SEQ ID NO: 19, Primer segni-cis-NdeF2
SEQ ID NO: 20, Primer lat-(Spe)AflR2
SEQ ID NO: 21, Primer loti-SD-PacF
SEQ ID NO: 22, Primer loti-AvrR
SEQ ID NO: 23, Nucleotide sequence of mutant cis
SEQ ID NO: 24, Amino acid sequence of the protein encoded by lat
SEQ ID NO: 25, Amino acid sequence of the protein encoded by cis
SEQ ID NO: 26, Amino acid sequence of the protein encoded by mutant cis
SEQ ID NO: 27, Primer proCrocGX-SpeR
SEQ ID NO: 28, Primer proCX-SpeR
SEQ ID NO: 29, Primer rocGX-SpeF
SEQ ID NO: 30, Primer proCX-SpeF

The invention claimed is:

1. A method for producing cis-5-hydroxy-L-pipecolic acid or a pharmacologically acceptable salt thereof, or a solvate thereof, which comprises a step of producing cis-5-hydroxy-L-pipecolic acid by using L-pipecolic acid as a substrate with a microorganism transformed with a heterologous polynucleotide selected from the group consisting of (A) to (F) in an expressible state:
   (A) a polynucleotide having the nucleotide sequence of SEQ ID NO: 2,
   (B) a polynucleotide hybridizable with a polynucleotide comprising the nucleotide sequence complementary to the nucleotide sequence of SEQ ID NO: 2 under stringent conditions, and encoding a protein having an activity of catalyzing a reaction of generating cis-5-hydroxy-L-pipecolic acid by using L-pipecolic acid as a substrate, wherein the stringent conditions comprise performing hybridization at 50° C. in the presence of a saline sodium citrate (SSC) solution of 2-fold concentration and 50% formamide followed by washing at 65° C. with an SSC solution of 0.1-fold concentration;
   (C) a polynucleotide showing an identity of 90% or higher to the nucleotide sequence of SEQ ID NO: 2, and encoding a protein having the activity of catalyzing the reaction of generating cis-5-hydroxy-L-pipecolic acid by using L-pipecolic acid as a substrate, wherein the polynucleotide comprises a partial sequence encoding an aspartyl/asparaginyl beta-hydroxylase region and a partial sequence encoding an L-proline 3-hydroxylase C-terminal region;
   (D) a polynucleotide encoding a protein having the amino acid sequence of SEQ ID NO: 25;
   (E) a polynucleotide encoding a protein having the amino acid sequence of SEQ ID NO: 25 including substitution, deletion, insertion, and/or addition of 30 or less amino acid residues, and having the activity of catalyzing the reaction of generating cis-5-hydroxy-L-pipecolic acid by using L-pipecolic acid as a substrate, wherein the polynucleotide comprises a partial sequence encoding an aspartyl/asparaginyl beta-hydroxylase region and a partial sequence encoding an L-proline 3-hydroxylase C-terminal region; and
   (F) a polynucleotide encoding a protein consisting of an amino acid sequence showing an identity of 90% or higher to the amino acid sequence of SEQ ID NO: 25, and having the activity of catalyzing the reaction of generating cis-5-hydroxy-L-pipecolic acid by using L-pipecolic acid as a substrate, wherein the polynucleotide comprises a partial sequence encoding an aspartyl/asparaginyl beta-hydroxylase region and a partial sequence encoding an L-proline 3-hydroxylase C-terminal region.

2. The production method according to claim 1, wherein the microorganism further comprises a polynucleotide encoding a protein having an activity of catalyzing a reaction of generating L-aminoadipate-delta-semialdehyde by using L-lysine as a substrate, and a polynucleotide encoding a protein having an activity of catalyzing a reaction of generating L-pipecolic acid by using delta-1-piperideine-6-carboxylic acid as a substrate, each in an expressible state; and
   the method further comprises a step of generating L-aminoadipate-delta-semialdehyde by using L-lysine as a substrate, and then converting L-aminoadipate-delta-semialdehyde into delta-1-piperideine-6-carboxylic acid; and
   a step of generating L-pipecolic acid by using delta-1-piperideine-6-carboxylic acid as a substrate.

3. The production method according to claim 2, wherein the polynucleotide encoding a protein having the activity of catalyzing the reaction of generating L-aminoadipate-delta-semialdehyde by using L-lysine as a substrate is derived from *Flavobacterium lutescens*.

4. The production method according to claim 2, wherein the microorganism is *Escherichia coli*, and comprises an endogenous polynucleotide encoding a protein having the activity of catalyzing the reaction of generating L-pipecolic acid by using delta-1-piperideine-6-carboxylic acid as a substrate.

5. A method for producing cis-5-hydroxy-L-pipecolic acid or a pharmacologically acceptable salt thereof, or a solvate thereof, which comprises a step of allowing a protein selected from the group consisting of (d) to (f) to act on L-pipecolic acid to generate cis-5-hydroxy-L-pipecolic acid:
  (d) a protein comprising the amino acid sequence of SEQ ID NO: 25;
  (e) a protein comprising the amino acid sequence of SEQ ID NO: 25 including a substitution, deletion, insertion, and/or addition of 30 or less amino acid residues, and having an activity of catalyzing a reaction of generating cis-5-hydroxy-L-pipecolic acid by using L-pipecolic acid as a substrate, wherein the protein comprises a partial sequence encoding an aspartyl/asparaginyl beta-hydroxylase region and a partial sequence encoding an L-proline 3-hydroxylase C-terminal region; and
  (f) a protein consisting of an amino acid sequence showing an identity of 90% or more to the amino acid sequence of SEQ ID NO: 25, and having the activity of catalyzing the reaction of generating cis-5-hydroxy-L-pipecolic acid by using L-pipecolic acid as a substrate, wherein the protein comprises a partial sequence of an aspartyl/asparaginyl beta-hydroxylase region and a partial sequence of an L-proline 3-hydroxylase C-terminal region.

6. The production method according to claim 5, which further comprises:
  a step of allowing a protein having an activity of catalyzing a reaction of generating L-aminoadipate-delta-semialdehyde by using L-lysine as a substrate to act on L-lysine to generate L-aminoadipate-delta-semialdehyde, and then converting L-aminoadipate-delta-semialdehyde into delta-1-piperideine-6-carboxylic acid; and
  a step of allowing a protein having an activity of catalyzing a reaction of generating L-pipecolic acid by using delta-1-piperideine-6-carboxylic acid as a substrate to act on the obtained delta-1-piperideine-6-carboxylic acid to generate L-pipecolic acid.

7. The production method according to claim 1, wherein the polynucleotide is selected from the group consisting of (A)-(D) and (F).

8. The method according to claim 1, wherein the polynucleotide is selected from the group consisting of a polynucleotide having the nucleotide sequence of SEQ ID NO: 2; a polynucleotide having the nucleotide sequence of SEQ ID NO: 23; a polynucleotide encoding a protein having the amino acid sequence of SEQ ID NO: 25; and a polynucleotide encoding a protein having the amino acid sequence of SEQ ID NO: 26.

9. The production method according to claim 5, wherein the protein is selected from the group consisting of (d) and (f).

10. The production method according to claim 5, wherein the protein is a protein consisting of an amino acid sequence showing an identity of 95% or more to the amino acid sequence of SEQ ID NO: 25, and having the activity of catalyzing the reaction of generating cis-5-hydroxy-L-pipecolic acid by using L-pipecolic acid as a substrate, wherein the protein comprises a partial sequence of an aspartyl/asparaginyl beta-hydroxylase region and a partial sequence of an L-proline 3-hydroxylase C-terminal region.

11. The production method according to claim 5, wherein the protein is selected from the group consisting of a protein comprising the amino acid sequence of SEQ ID NO: 25 and a protein comprising the amino acid sequence of SEQ ID NO: 26.

12. A method for producing cis-5-hydroxy-L-pipecolic acid or a pharmacologically acceptable salt thereof, or a solvate thereof, which comprises a step of producing cis-5-hydroxy-L-pipecolic acid by using L-pipecolic acid as a substrate with a microorganism transformed with a heterologous polynucleotide selected from the group consisting of (A)-(D) and (F) in a expressible state:
  (A) a polynucleotide having the nucleotide sequence of SEQ ID NO: 2,
  (B) a polynucleotide hybridizable with a polynucleotide comprising the nucleotide sequence complementary to the nucleotide sequence of SEQ ID NO: 2 under stringent conditions, and encoding a protein having an activity of catalyzing a reaction of generating cis-5-hydroxy-L-pipecolic acid by using L-pipecolic acid as a substrate, wherein the stringent conditions comprise performing hybridization at 50° C. in the presence of a saline sodium citrate (SSC) solution of 2-fold concentration and 50% formamide followed by washing at 65° C. with an SSC solution of 0.1-fold concentration;
  (C) a polynucleotide showing an identity of 95% or higher to the nucleotide sequence of SEQ ID NO: 2, and encoding a protein having the activity of catalyzing the reaction of generating cis-5-hydroxy-L-pipecolic acid by using L-pipecolic acid as a substrate, wherein the polynucleotide comprises a sequence encoding an aspartyl/asparaginyl beta-hydroxylase region comprising residues 26-174 of SEQ ID NO: 25 and a sequence encoding an L-proline 3-hydroxylase C-terminal region comprising residues 190-274 of SEQ ID NO: 25;
  (D) a polynucleotide encoding a protein having the amino acid sequence of SEQ ID NO: 25;
  (F) a polynucleotide encoding a protein consisting of an amino acid sequence showing an identity of 95% or higher to the amino acid sequence of SEQ ID NO: 25, and having the activity of catalyzing the reaction of generating cis-5-hydroxy-L-pipecolic acid by using L-pipecolic acid as a substrate, wherein the polynucleotide comprises a sequence encoding an aspartyl/asparaginyl beta-hydroxylase region comprising residues 26-174 of SEQ ID NO: 25 and a sequence encoding an L-proline 3-hydroxylase C-terminal region comprising residues 190-274 of SEQ ID NO: 25.

13. The production method according to claim 12, wherein the microorganism further comprises a polynucleotide encoding a protein having an activity of catalyzing a reaction of generating L-aminoadipate-delta-semialdehyde by using L-lysine as a substrate, and a polynucleotide encoding a protein having an activity of catalyzing a reaction of generating L-pipecolic acid by using delta-1-piperideine-6-carboxylic acid as a substrate, each in an expressible state; and
  the method further comprises a step of generating L-aminoadipate-delta-semialdehyde by using L-lysine as a substrate, and then converting L-aminoadipate-delta-semialdehyde into delta-1-piperideine-6-carboxylic acid; and
  a step of generating L-pipecolic acid by using delta-1-piperideine-6-carboxylic acid as a substrate.

14. The production method according to claim 12, wherein the polynucleotide encoding a protein having the activity of catalyzing the reaction of generating L-aminoadipate-delta-semialdehyde by using L-lysine as a substrate is derived from *Flavobacterium lutescens*.

15. The production method according to claim 12, wherein the microorganism is *Escherichia coli*, and comprises an endogenous polynucleotide encoding a protein having the activity of catalyzing the reaction of generating L-pipecolic acid by using delta-1-piperideine-6-carboxylic acid as a substrate.

* * * * *